US008592051B2

(12) United States Patent
Funahashi

(10) Patent No.: US 8,592,051 B2
(45) Date of Patent: *Nov. 26, 2013

(54) AROMATIC AMINE DERIVATIVE AND ORGANIC ELECTROLUMINESCENT ELEMENT MADE WITH THE SAME

(75) Inventor: Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 896 days.

This patent is subject to a terminal disclaimer.

(21) Appl. No.: 10/549,801

(22) PCT Filed: Mar. 8, 2004

(86) PCT No.: PCT/JP2004/002945
§ 371 (c)(1),
(2), (4) Date: Nov. 21, 2005

(87) PCT Pub. No.: WO2004/083162
PCT Pub. Date: Sep. 30, 2004

(65) Prior Publication Data
US 2007/0009758 A1   Jan. 11, 2007

(30) Foreign Application Priority Data
Mar. 20, 2003   (JP) ................................ 2003-076772

(51) Int. Cl.
*H01L 51/54*   (2006.01)
(52) U.S. Cl.
USPC ............ 428/690; 428/917; 313/504; 313/506
(58) Field of Classification Search
USPC ............. 313/504, 506; 257/E51.05, E51.051; 564/426, 434
See application file for complete search history.

(56) References Cited

U.S. PATENT DOCUMENTS

| 4,233,384 | A | * | 11/1980 | Turner et al. ............... 430/58.75 |
|---|---|---|---|---|
| 5,153,073 | A | | 10/1992 | Ohnuma et al. .............. 428/461 |
| 5,281,489 | A | * | 1/1994 | Mori et al. ................... 428/690 |
| 5,817,739 | A | * | 10/1998 | Nukada et al. ............... 528/292 |
| 6,280,859 | B1 | * | 8/2001 | Onikubo et al. .............. 428/690 |
| 6,661,023 | B2 | * | 12/2003 | Hoag et al. ....................... 257/40 |
| 7,651,786 | B2 | * | 1/2010 | Matsuura et al. ............. 428/690 |
| 7,705,183 | B2 | * | 4/2010 | Funahashi et al. ............ 564/308 |
| 7,732,063 | B2 | * | 6/2010 | Matsuura et al. ............. 428/690 |
| 2003/0118866 | A1 | * | 6/2003 | Oh et al. ........................ 428/690 |
| 2003/0157364 | A1 | * | 8/2003 | Senoo et al. .................. 428/690 |
| 2004/0053069 | A1 | | 3/2004 | Sotoyama et al. ............ 428/690 |
| 2004/0137270 | A1 | | 7/2004 | Seo et al. ...................... 428/690 |
| 2005/0064233 | A1 | | 3/2005 | Matsuura et al. ............. 428/690 |
| 2005/0227111 | A1 | | 10/2005 | Hosokawa et al. ........... 428/690 |
| 2006/0033421 | A1 | | 2/2006 | Matsuura et al. ............. 313/499 |
| 2007/0237984 | A1 | | 10/2007 | Matsuura et al. ............. 428/690 |
| 2011/0297923 | A1 | | 12/2011 | Mizuki et al. |
| 2012/0056165 | A1 | | 3/2012 | Kawamura et al. |

FOREIGN PATENT DOCUMENTS

| EP | 0 710 893 | | 5/1996 |
|---|---|---|---|
| EP | 1437395 | * | 7/2004 |
| JP | 04020573 | | 1/1992 |
| JP | 04036264 | | 2/1992 |
| JP | 04-118658 | | 4/1992 |
| JP | 04-133064 | | 5/1992 |
| JP | 4-175395 | | 6/1992 |
| JP | 05-021161 | * | 1/1993 |
| JP | 06-240248 | | 8/1994 |
| JP | 07-157754 | | 6/1995 |
| JP | 08-176293 | | 7/1996 |
| JP | 08199162 | | 8/1996 |
| JP | 08-302341 | | 11/1996 |
| JP | 10088122 | | 4/1998 |
| JP | 10-251633 | | 9/1998 |
| JP | 10-265773 | | 10/1998 |
| JP | 2003-005392 | | 1/2003 |
| KR | 10-2011-0094271 A | | 8/2011 |
| KR | 10-2011-0103974 A | | 9/2011 |
| WO | WO 2004/018588 A1 | | 3/2004 |

OTHER PUBLICATIONS

Translation for JP 05-021161, published Jan. 1993.*
Translation for JP 10-88122, published Apr. 1998.*
Request issued Nov. 29, 2012 in Korean Patent Application No. 2012-002828.
Opinion issued Sep. 2, 2013 in Korean Patent Application No. 2012-002828.

* cited by examiner

*Primary Examiner* — Dawn L. Garrett
(74) *Attorney, Agent, or Firm* — Oblon, Spivak, McClelland, Maier & Neustadt, L.L.P.

(57) ABSTRACT

The present invention relates to aromatic amine derivatives having a specific structure in which a substituted diphenylamino group is bonded to a pyrene structure; and organic electroluminescent devices comprising a cathode, an anode and one or plural organic thin film layers having at least a light emitting layer which are sandwiched between the cathode and the anode wherein at least one of the organic thin film layers contains the above material for organic electroluminescent devices in the form of a single substance or a component of a mixture. There are provided the material for organic electroluminescent devices exhibiting a long lifetime and a high efficiency of blue light emission, as well as the aromatic amine derivatives capable of realizing such organic electroluminescent devices.

18 Claims, 6 Drawing Sheets

AROMATIC AMINE DERIVATIVE AND ORGANIC ELECTROLUMINESCENT ELEMENT MADE WITH THE SAME

TECHNICAL FIELD

The present invention relates to organic electroluminescent devices which are used as a surface light-emitting member of wall-type televisions or a light source such as a backlight for displays, and exhibit a long service life and a high efficiency of light emission, as well as novel aromatic amine derivatives capable of realizing such electroluminescent devices.

BACKGROUND ART

Organic electroluminescent (EL) devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices requires high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices operable at low driving voltage, with excellent luminance and favorable efficiency of light emission.

For example, there is disclosed such a technique using a single monoanthracene compound as an organic light-emitting material (Japanese Unexamined Patent Application Laid-Open No. Hei 11-3782A). However, in this technique, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technique using a single bisanthracene compound as an organic light emitting material (Japanese Unexamined Patent Application Laid-Open No. Hei 8-12600). However, in this technique, an efficiency of light emission obtained by using the material is also as low as about 1 to 3 cd/A. Therefore, further improvement of the technique has bee demanded for rendering it practically usable. Further, there is disclosed a technique using a mono- or bis-anthracene compound together with a distearyl compound in an organic light emitting medium layer (International Application Published under PCT No. WO 00/06402). However, the device described therein fails to show a sufficiently long half lifetime and, therefore, further improvement has been demanded therefor.

DISCLOSURE OF THE INVENTION

The present invention has been made to solve the above problems. An object of the present invention is to provide organic EL devices having a long service life and a high efficiency of light emission, and aromatic amine derivatives capable of realizing such organic EL devices.

As a result of extensive researches for developing aromatic amine derivatives having the above suitable properties and organic EL devices using the aromatic amine derivatives, the inventors have found that the object of the present invention can be achieved by using aromatic amine derivatives represented by any one of the following general formulae (I) to (III) and (I') to (III') in which a substituted diphenyl amino group is bonded to a pyrene structure. The present invention has been accomplished on the basis of the above finding.

Thus, the present invention provides an aromatic amine derivative represented by any of the following general formulae (I) to (III) and (I') to (III'):

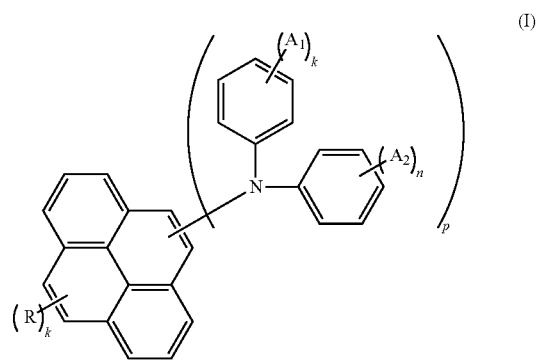

wherein R is a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a cyano group or a halogen atom; k is an integer of 1 to 9, and when k is 2 or more, a plurality of R groups may be the same with or different from each other;

$A^1$ and $A^2$ are each independently a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a cyano group or a halogen atom; m and n are each an integer of 0 to 5 wherein when m is 2 or more, a plurality of $A^1$ groups may be the same with or different from each other and may be bonded to each other to form an saturated or unsaturated ring, and when n is 2 or more, a plurality of $A^2$ groups may be the same with or different from each other and may be bonded to each other to form an saturated or unsaturated ring, with the proviso that at least one of $A^1$ and $A^2$ contains any of a substituted or unsubstituted alkyl group having 2 or more carbon atoms, a substituted or unsubstituted aralkyl group having 2 or more carbon atoms, a substituted or unsubstituted cycloalkyl group having 3 or more carbon atoms, a substituted or unsubstituted alkoxy group having 2 or more carbon atoms and a substituted or unsubstituted alkylamino group having 2 or more carbon atoms; and p is an integer of 1 to 9, and when p is 2 or more, a plurality of groups being represented within the parenthesis ( )$_p$ of the general formula (I) may be the same with or different from each other, and (k+p) is an integer of 10 or smaller.

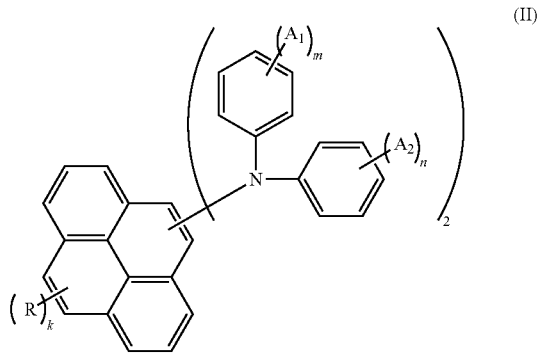
(II)

wherein R, A$^1$ and A$^2$, and k, m and n are the same as defined in the general formula (I), and two groups being represented within the parenthesis ( )$_2$ of the general formula (II) may be the same with or different from each other.

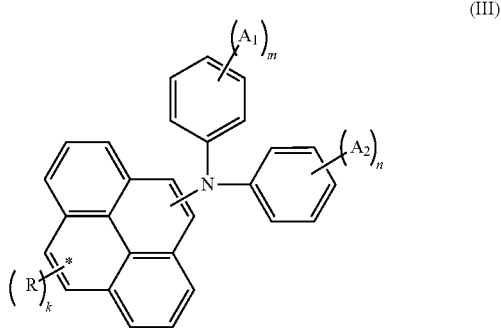
(III)

wherein R, A$^1$ and A$^2$, and k, m and n are the same as defined in the general formula (I).

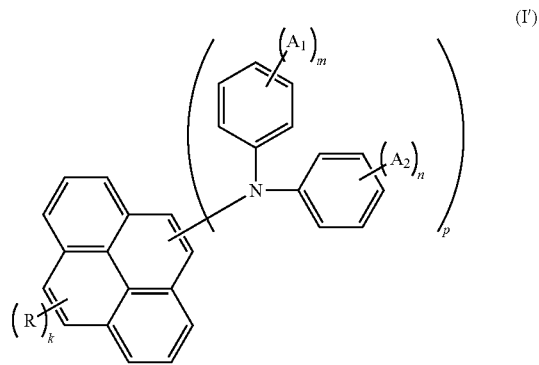
(I')

wherein R is a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a cyano group or a halogen atom; k is an integer of 1 to 9, and when k is 2 or more, a plurality of R groups may be the same with or different from each other;

A$^1$ and A$^2$ are each independently a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a cyano group or a halogen atom; m and n are each an integer of 0 to 5 wherein when m is 2 or more, a plurality of A$^1$ groups may be the same with or different from each other and may be bonded to each other to form an saturated or unsaturated ring, and when n is 2 or more, a plurality of A$^2$ groups may be the same with or different from each other and may be bonded to each other to form an saturated or unsaturated ring, with the proviso that at least one of m and n is an integer of 2 or more; and p is an integer of 1 to 9, and when p is 2 or more, a plurality of groups being represented within the parenthesis ( )$_p$ of the general formula (I') may be the same with or different from each other, and (k+p) is an integer of 10 or smaller.

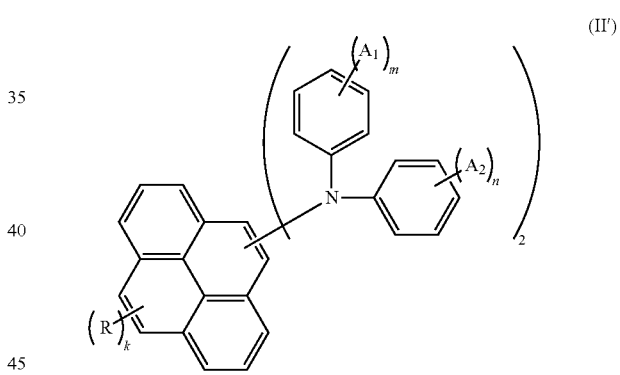
(II')

wherein R, A$^1$ and A$^2$, and k, m and n are the same as defined in the general formula (I'), and two groups being represented within the parenthesis ( )$_2$ of the general formula (II') may be the same with or different from each other.

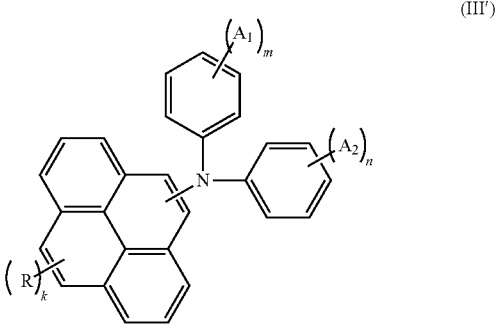
(III')

wherein R, A¹ and A², and k, m and n are the same as defined in the general formula (I').

Also, the present invention provides:

An organic electroluminescent device comprising a cathode, an anode and one or plural organic thin film layers having at least a light emitting layer which are sandwiched between the cathode and the anode, wherein at least one of the organic thin film layers contains the aromatic amine derivative represented by any of the above general formulae (I) to (III) and (I') to (III') in the form of a single substance or a component of a mixture;

an organic electroluminescent device comprising a cathode, an anode and two or more organic thin film layers having at least a light emitting layer which are sandwiched between the cathode and the anode, wherein the organic thin film layers include an organic layer containing the aromatic amine derivative represented by any of the above general formulae (I) to (III) and (I') to (III') as a main component which is provided between the anode and the light emitting layer; and an organic electroluminescent device comprising a cathode, an anode and one or plural organic thin film layers having at least a light emitting layer which are sandwiched between the cathode and the anode, wherein the light emitting layer contains the aromatic amine derivative represented by any of the above general formulae (I) to (III) and (I') to (III') in an amount of 0.1 to 20% by weight.

BEST MODE FOR CARRYING OUT THE INVENTION

Figure 1:
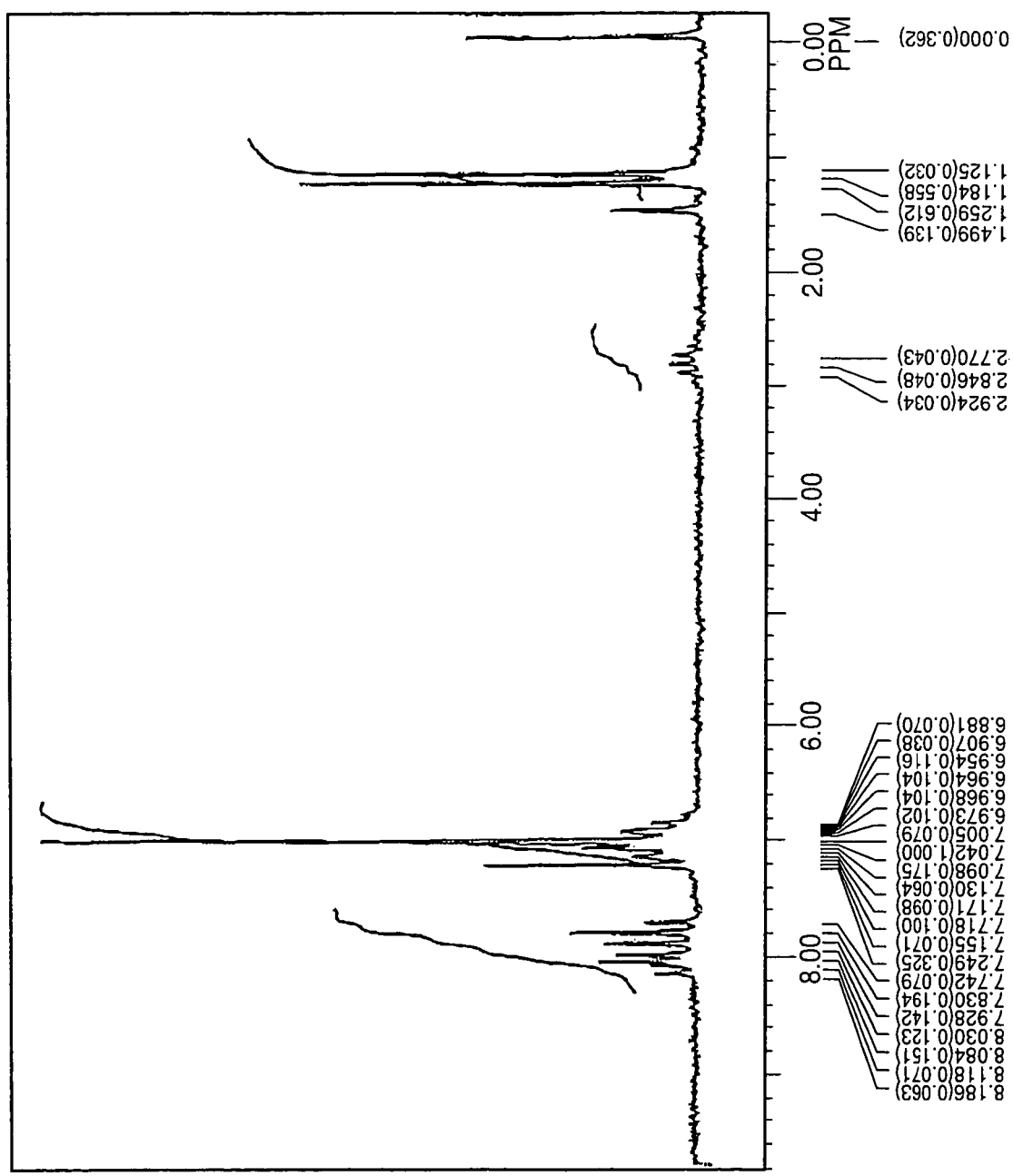
FIG. 1 is a chart showing Nuclear Magnetic Resonance (NMR) spectrum of the compound (8) as the aromatic amine derivative of the present invention.

The aromatic amine derivative of the present invention is represented by any of the above general formulae (I) to (III) and (I') to (III').

In the general formulae (I) to (III) and (I') to (III'), R represents a hydrogen atom; a substituted or unsubstituted alkyl group having 1 to 50 carbon atoms and preferably 1 to 20 carbon atoms; a substituted or unsubstituted aryl group having 5 to 50 carbon atoms and preferably 5 to 20 carbon atoms; a substituted or unsubstituted aralkyl group having 1 to 50 carbon atoms and preferably 9 to 20 carbon atoms; a substituted or unsubstituted cycloalkyl group having 3 to 50 carbon atoms and preferably 5 to 12 carbon atoms; a substituted or unsubstituted alkoxy group having 1 to 50 carbon atoms and preferably 1 to 6 carbon atoms; a substituted or unsubstituted aryloxy group having 5 to 50 carbon atoms and preferably 5 to 18 carbon atoms; a substituted or unsubstituted arylamino group having 5 to 50 carbon atoms and preferably 5 to 18 carbon atoms; a substituted or unsubstituted alkylamino group having 1 to 20 carbon atoms and preferably 1 to 6 carbon atoms; a cyano group; or a halogen atom.

Examples of the alkyl group as R include methyl, ethyl, propyl, isopropyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphneylmethyl and α-benzyloxybenzyl.

Examples of the aryl group as R include phenyl, 2-methylphenyl, 3-methylphenyl, 4-methylphenyl, 4-ethylphenyl, biphenyl, 4-methyl biphenyl, 4-ethyl biphenyl, 4-cyclohexyl biphenyl, terphenyl, 3,5-dichlorophenyl, naphthyl, 5-methyl naphthyl, anthryl and pyrenyl.

Examples of the aralkyl group as R include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl.

Examples of the cycloalkyl group as R include cyclopropyl, cyclobutyl, cyclopentyl, cyclohexyl, a norbornene group and adamantyl.

Examples of the alkoxy group as R include methoxy, ethoxy, propoxy, isopropoxy, butoxy, isobutoxy, sec-butoxy, tert-butoxy, various pentyloxy groups and various hexyloxy groups.

Examples of the aryloxy group as R include phenoxy, tolyloxy and naphthyloxy.

Examples of the arylamino group as R include diphenylamino, ditolylamino, isopropyldiphenylamino, t-butyldiphenylamino, diisopropyldiphenylamino, di-t-butyldiphenylamino, dinaphthylamino and naphthylphenylamino.

Examples of the alkylamino group as R include dimethylamino, diethylamino and dihexylamino.

Examples of the halogen atom as R include fluorine, chlorine, bromine, etc.

In the general formulae (I) to (III) and (I') to (III'), k is an integer of 1 to 9 and preferably 1 to 3, and when k is 2 or more, a plurality of R groups may be the same with or different from each other.

In the general formulae (I) to (III) and (I') to (III'), A¹ and A² are each independently a hydrogen atom; a substituted or unsubstituted alkyl group having 1 to 50 carbon atoms and preferably 1 to 20 carbon atoms; a substituted or unsubstituted aryl group having 5 to 50 carbon atoms and preferably 5 to 20 carbon atoms; a substituted or unsubstituted aralkyl group having 1 to 50 carbon atoms and preferably 9 to 20 carbon atoms; a substituted or unsubstituted cycloalkyl group having 3 to 50 carbon atoms and preferably 5 to 12 carbon atoms; a substituted or unsubstituted alkoxy group having 1 to 50 carbon atoms and preferably 1 to 6 carbon atoms; a substituted or unsubstituted aryloxy group having 5 to 50 carbon atoms and preferably 5 to 18 carbon atoms; a substituted or unsubstituted arylamino group having 5 to 50 carbon atoms and preferably 5 to 18 carbon atoms; a substituted or unsubstituted alkylamino group having 1 to 20 carbon atoms and preferably 1 to 6 carbon atoms; a cyano group; or a halogen atom.

Specific examples of the alkyl, aryl, aralkyl, cycloalkyl, alkoxy, aryloxy, arylamino and alkylamino groups as well as the halogen atom as $A^1$ and $A^2$ include the same as those exemplified as R above.

In the general formulae (I) to (III) and (I') to (III'), m and n are each an integer of 0 to 5 and preferably 0 to 2.

When m is 2 or more, a plurality of $A^1$ groups may be the same with or different from each other and may be bonded to each other to form an saturated or unsaturated ring. Also, when n is 2 or more, a plurality of $A^2$ groups may be the same with or different from each other and may be bonded to each other to form an saturated or unsaturated ring, However, in the general formulae (I) to (III), it is required to satisfy such a condition that at least one of $A^1$ and $A^2$ contains any of a substituted or unsubstituted alkyl group having 2 or more carbon atoms, a substituted or unsubstituted aralkyl group having 2 or more carbon atoms, a substituted or unsubstituted cycloalkyl group having 3 or more carbon atoms, a substituted or unsubstituted alkoxy group having 2 or more carbon atoms and a substituted or unsubstituted alkylamino group having 2 or more carbon atoms, and at least one of $A^1$ and $A^2$ preferably contains any of a substituted or unsubstituted branched alkyl group having 3 or more carbon atoms, a substituted or unsubstituted branched aralkyl group having 3 or more carbon atoms, a substituted or unsubstituted cycloalkyl group having 3 or more carbon atoms, a substituted or unsubstituted branched alkoxy group having 3 or more carbon atoms and a substituted or unsubstituted alkylamino group having 2 or more carbon atoms.

Further, in the general formulae (I') to (III'), at least one of m an n is an integer of 2 or more.

In the general formulae (I) and (I'), p is an integer of 1 to 9, preferably 1 to 4 and more preferably 1 to 2. When p is 2 or more, a plurality of groups being represented within the parenthesis ( )$_p$ of the general formula (I) and (I') may be the same with or different from each other, and a sum of k and p (k+p) is an integer of 10 or less and preferably 2 to 7. In the general formulae (II) and (II'), the two groups being represented within the parenthesis ( )$_2$ thereof may be the same with or different from each other.

Among the aromatic amine derivatives represented by the general formula (I), especially preferred are those represented by the general formulae (II) and (III). Among the aromatic amine derivatives represented by the general formula (I'), especially preferred are those represented by the general formulae (II') and (III').

Specific examples of the aromatic amine derivatives represented by the general formulae (I) to (III) and (I') to (III') include compounds (1) to (69) enumerated below, though not particularly limited thereto. Meanwhile, in the following compounds, Me represents a methyl group.

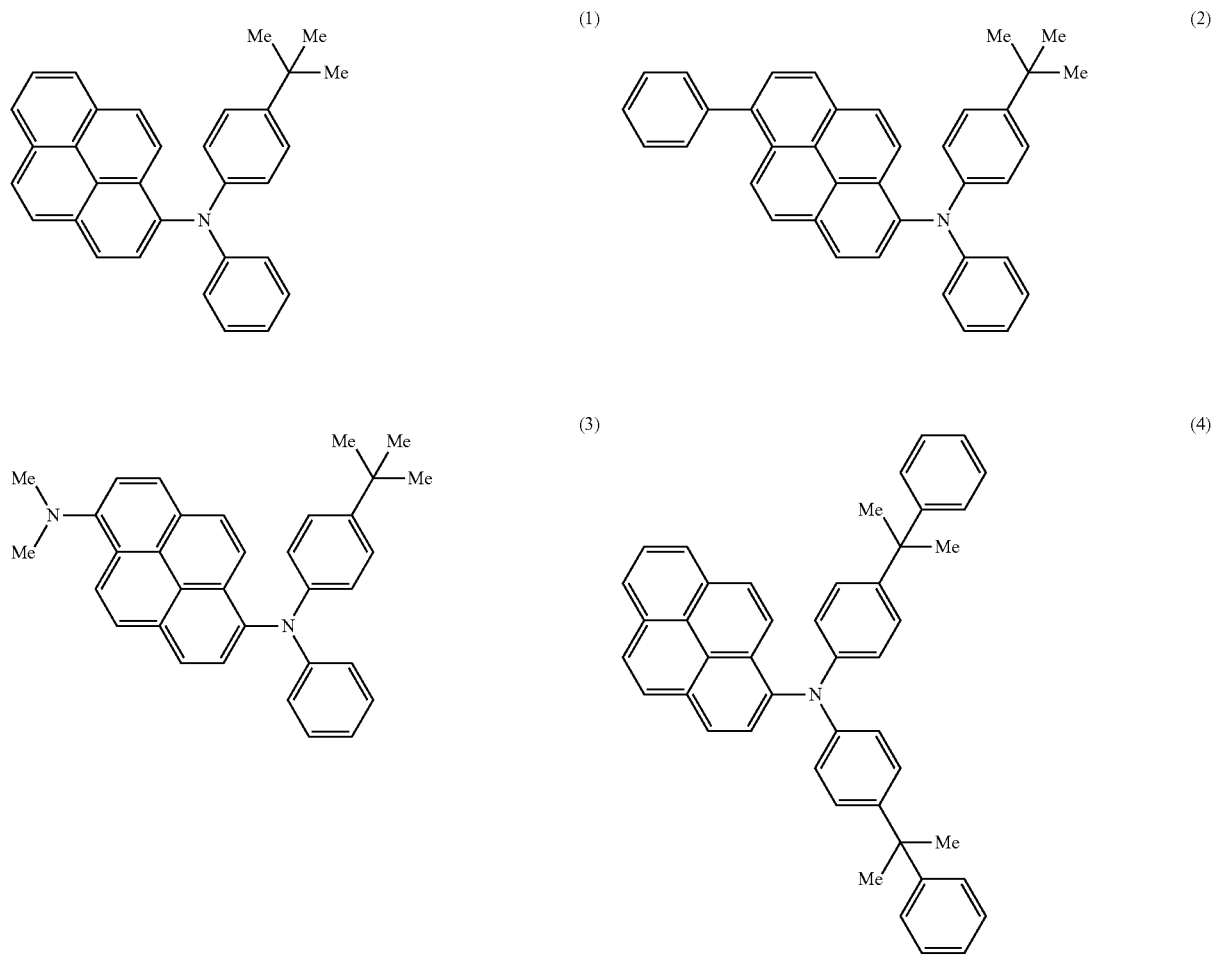

-continued
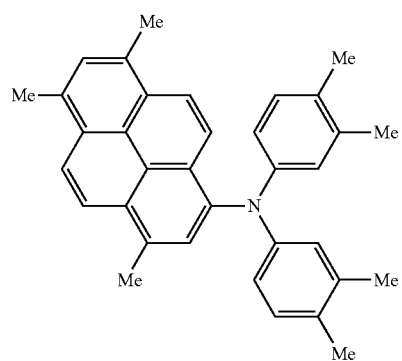
(5)
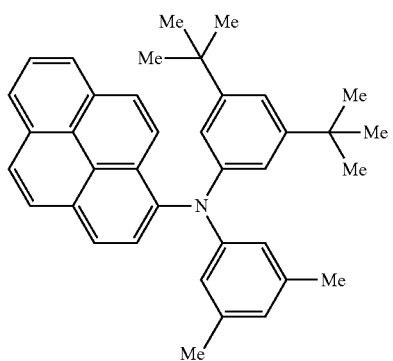
(6)
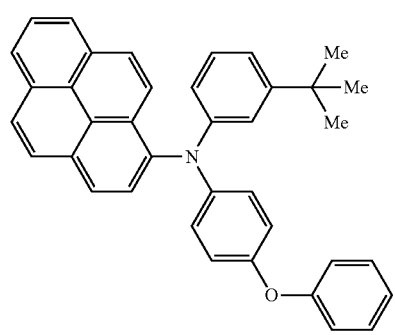
(7)
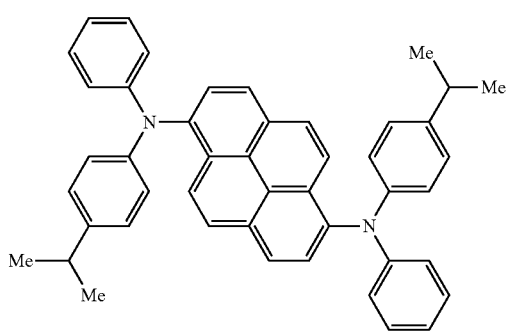
(8)
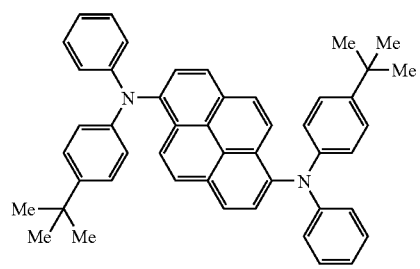
(9)
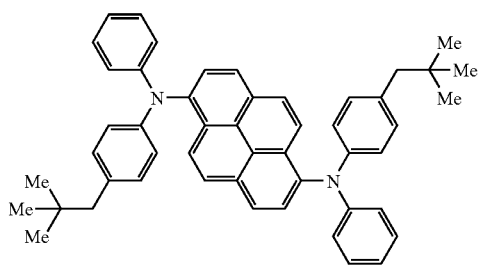
(10)
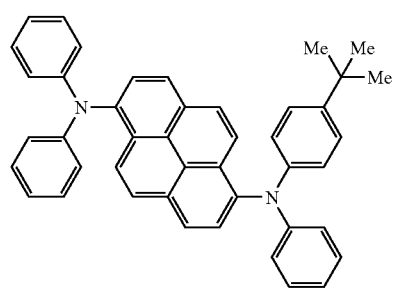
(11)
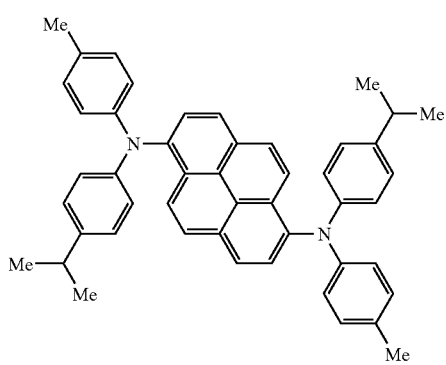
(12)

-continued
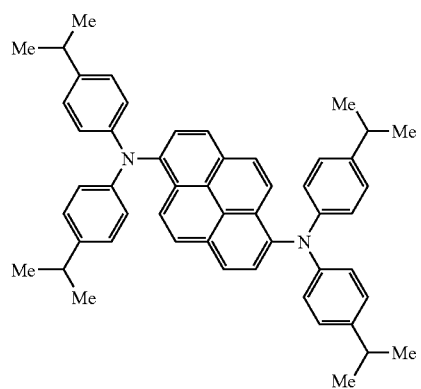 (13)
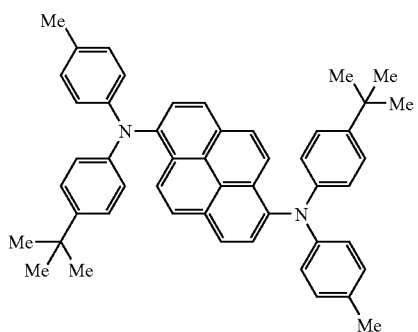 (14)
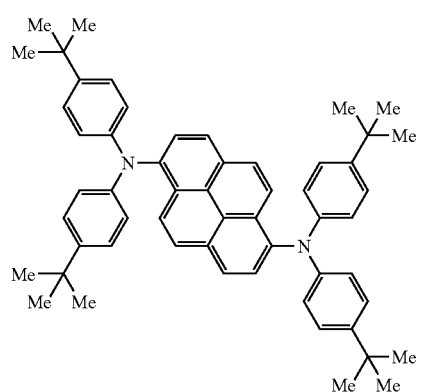 (15)
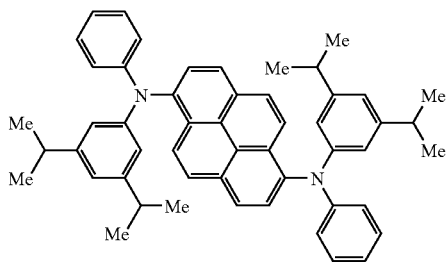 (16)
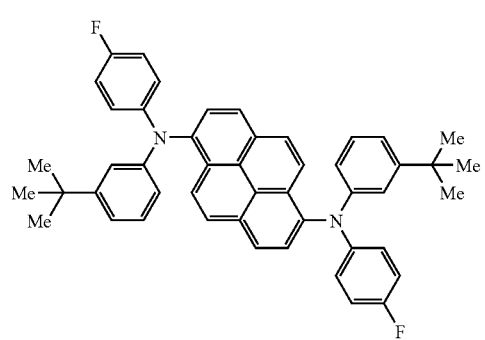 (17)
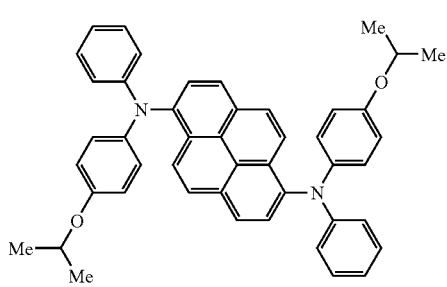 (18)
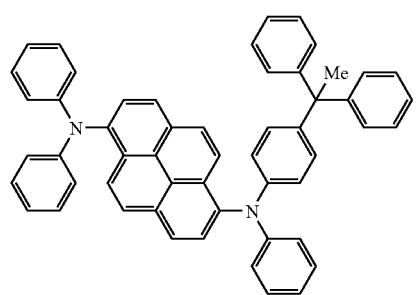 (19)
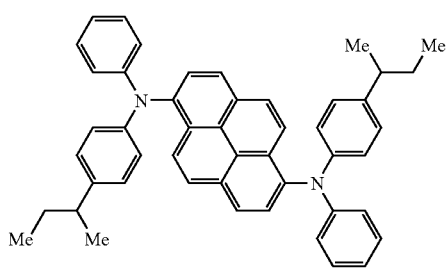 (20)

-continued
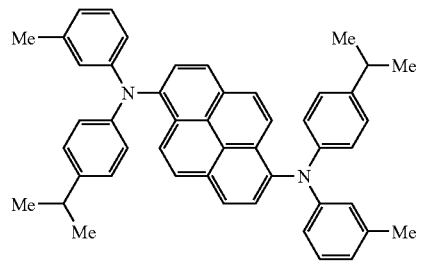
(21)
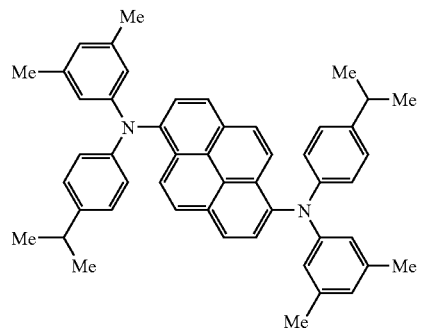
(22)
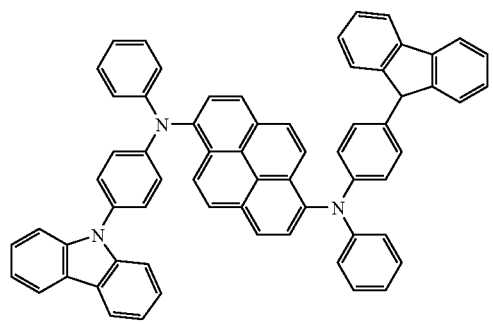
(23)
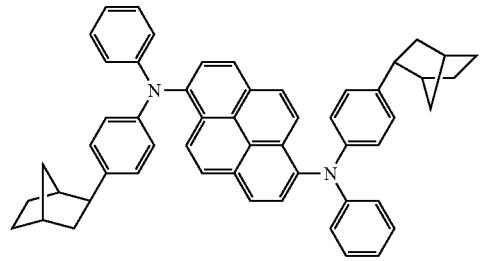
(24)
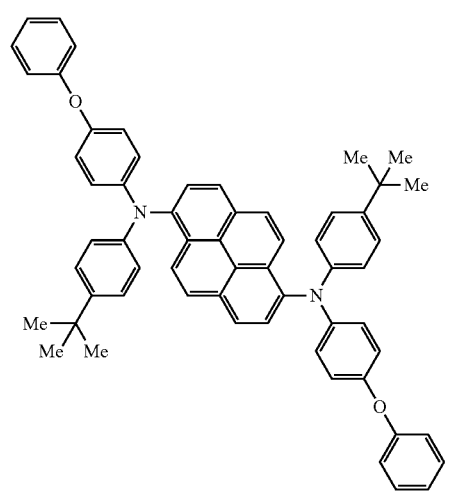
(25)
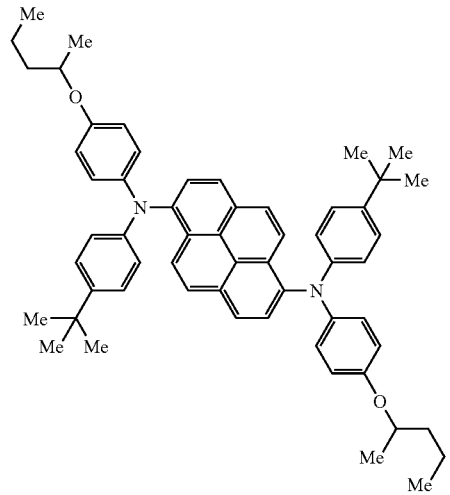
(26)
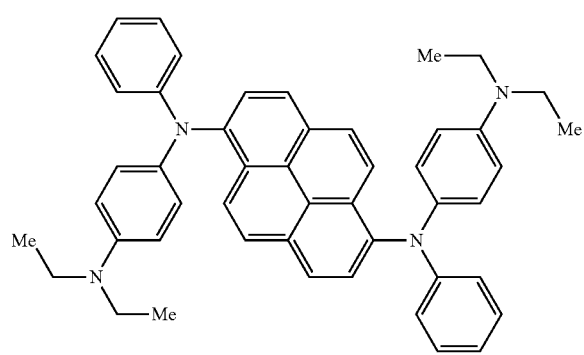
(27)
(28)

-continued
(29)
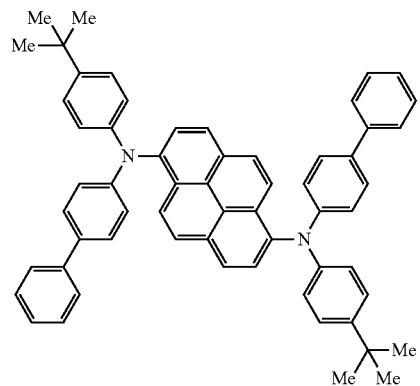
(30)
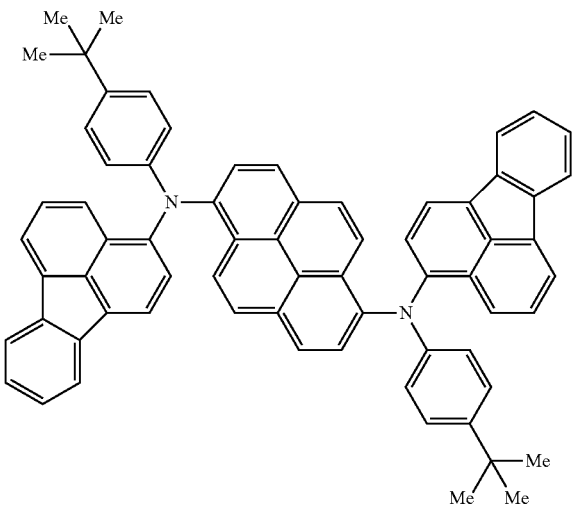
(31)
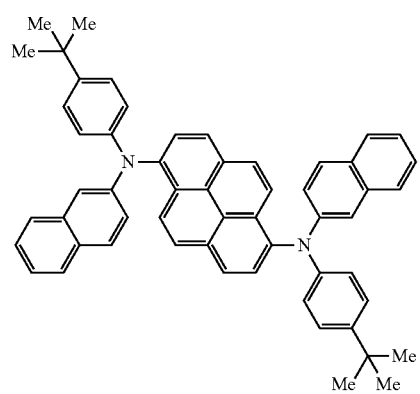
(32)
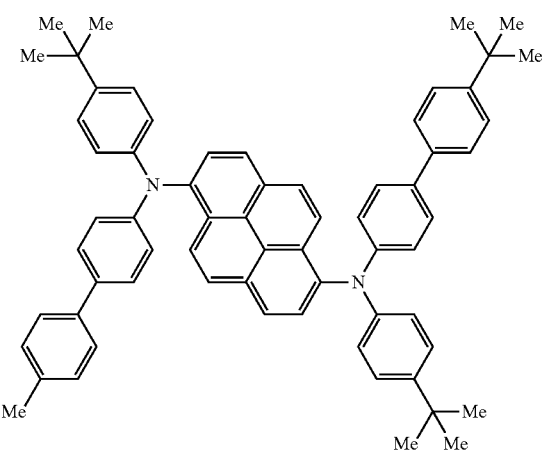
(33)
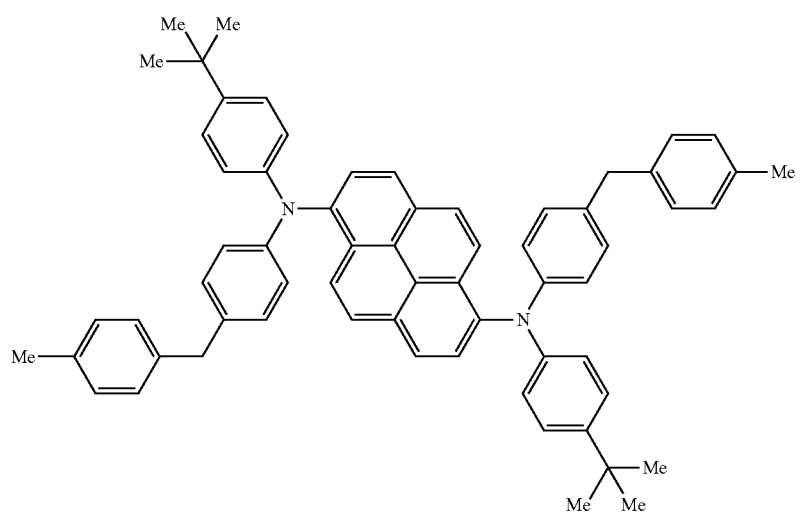

-continued
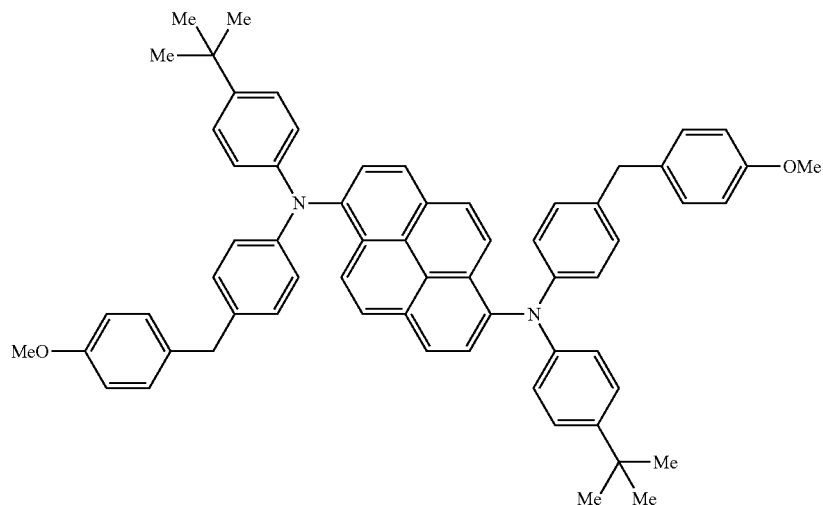
(34)
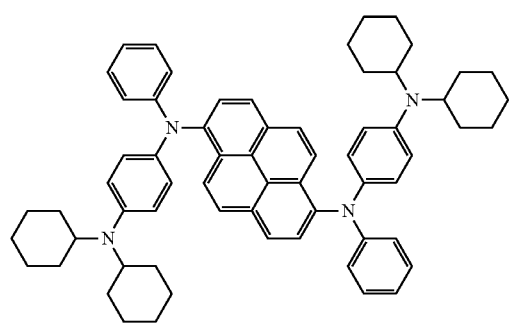
(35)
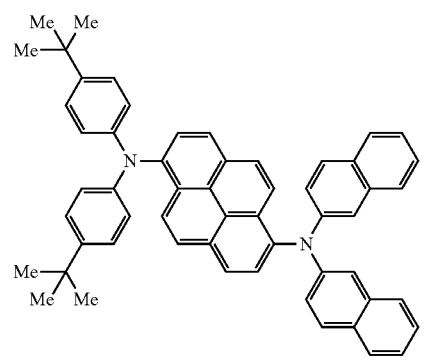
(36)
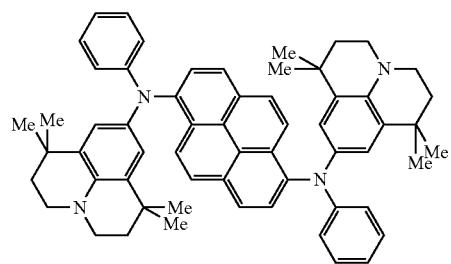
(37)
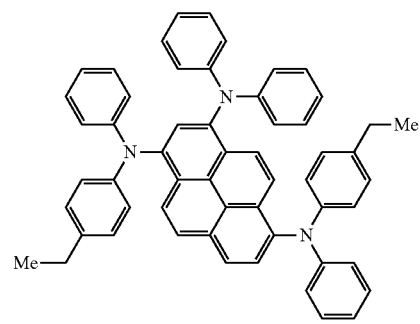
(38)
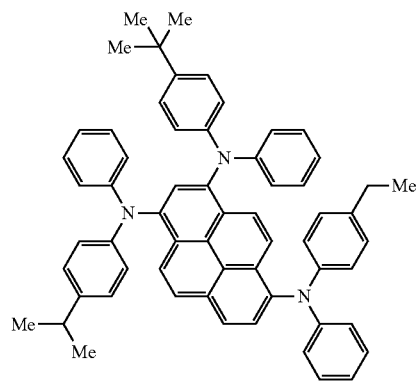
(39)
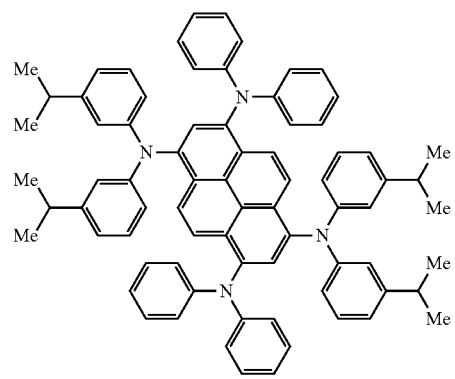
(40)

-continued
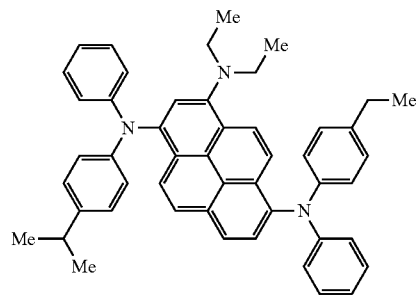
(41)
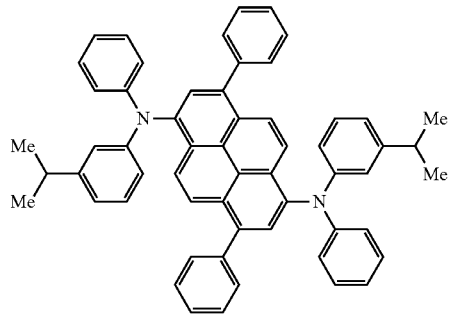
(42)
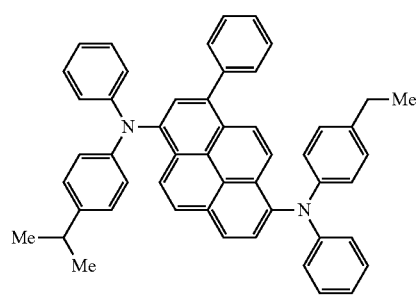
(43)
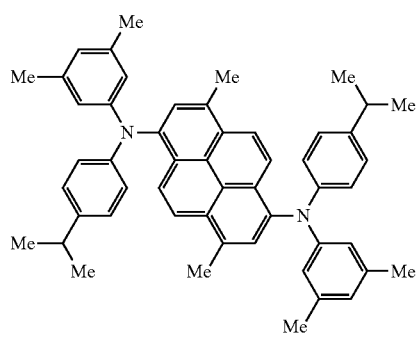
(44)
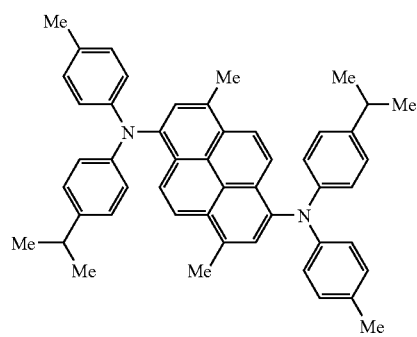
(45)
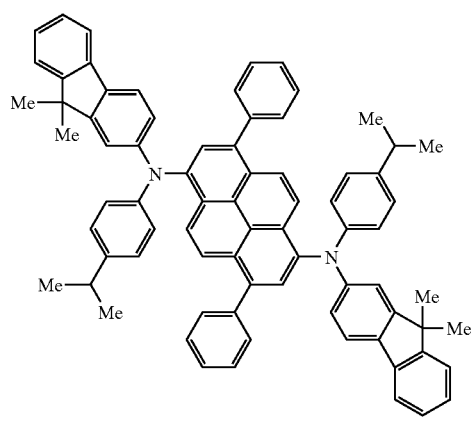
(46)
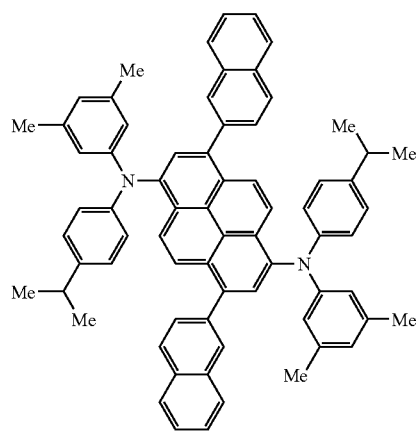
(47)
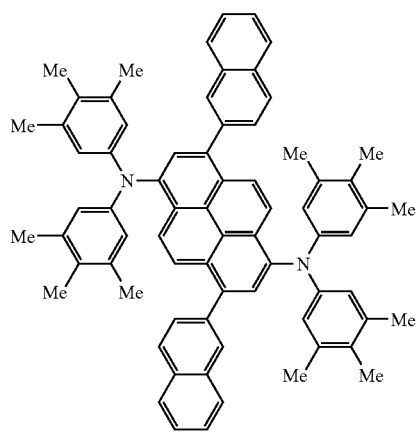
(48)

-continued
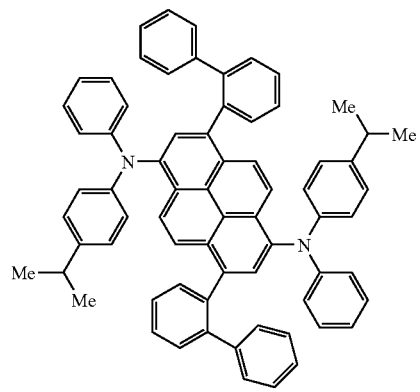
(49)
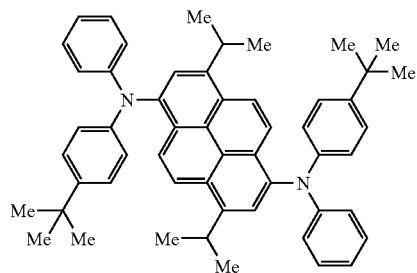
(50)
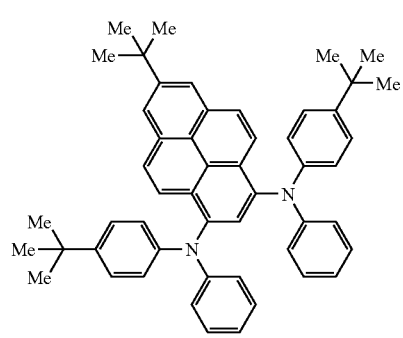
(51)
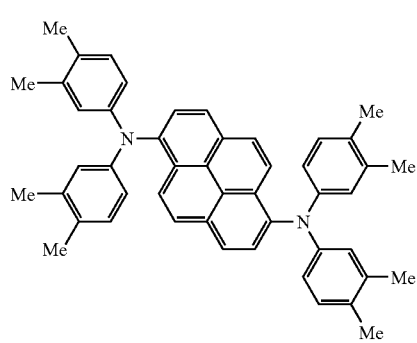
(52)
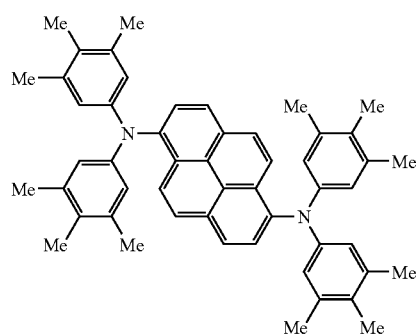
(53)
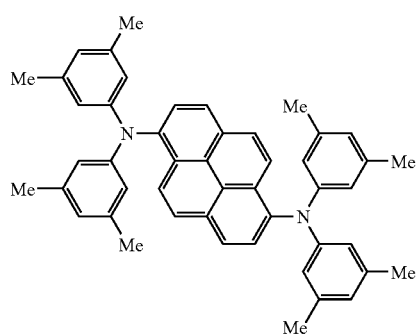
(54)
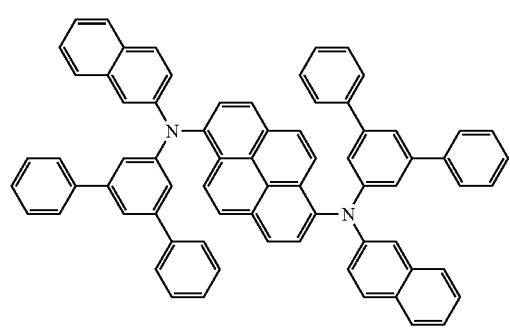
(55)
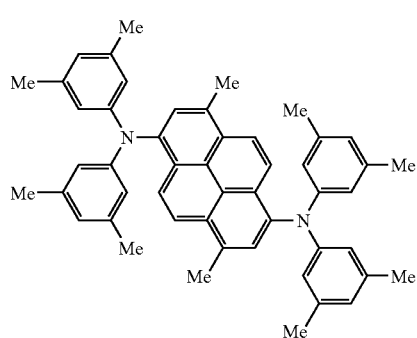
(56)

-continued
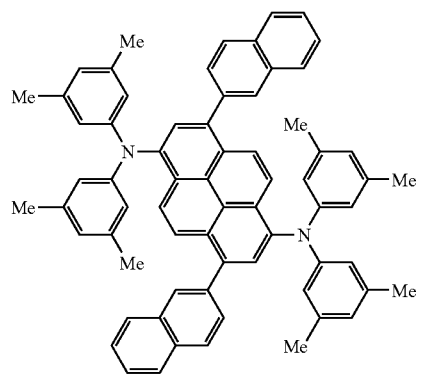
(57)
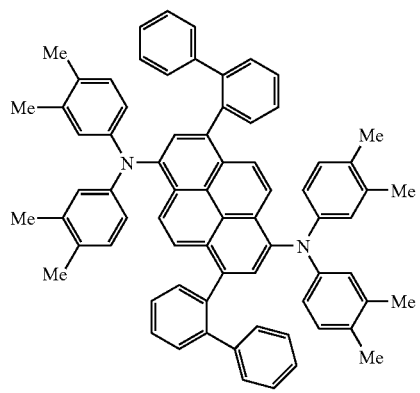
(58)
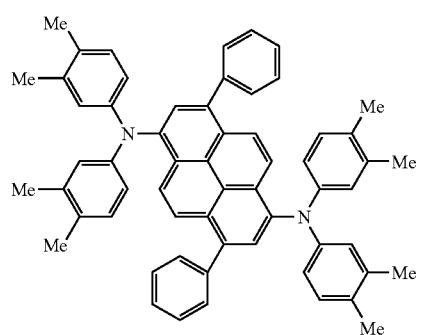
(59)
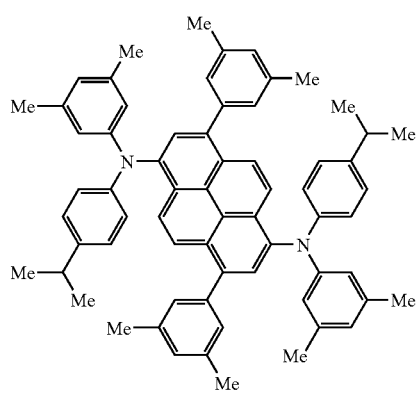
(60)
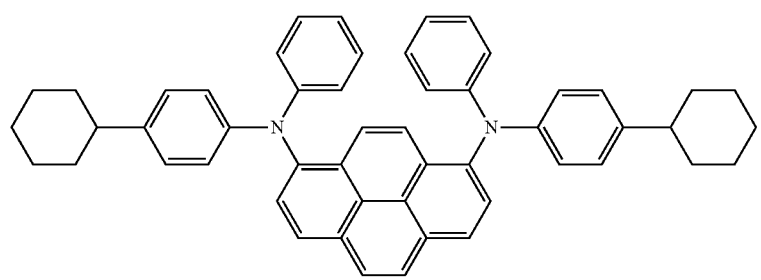
(61)
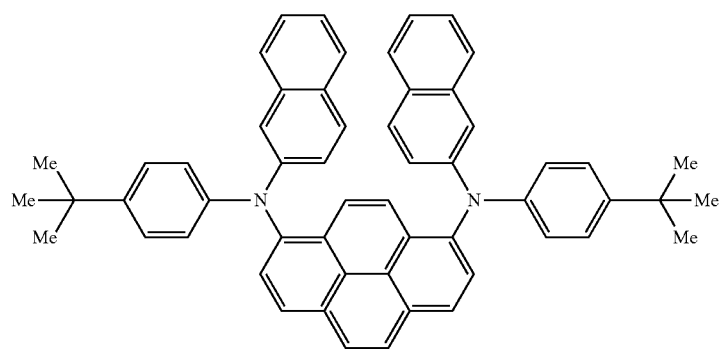
(62)

-continued
(63)
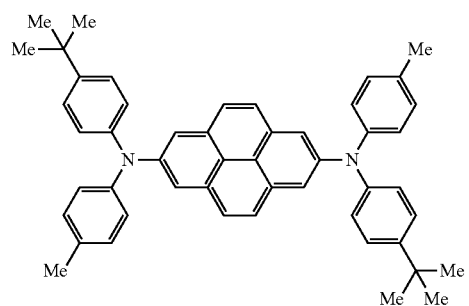
(61)
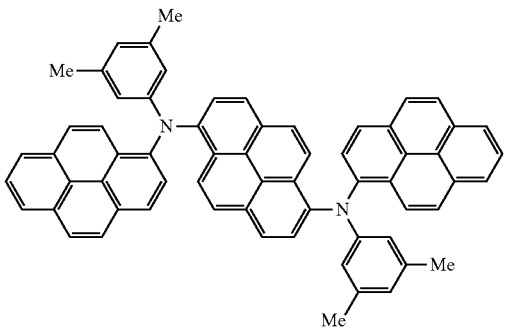
(62)
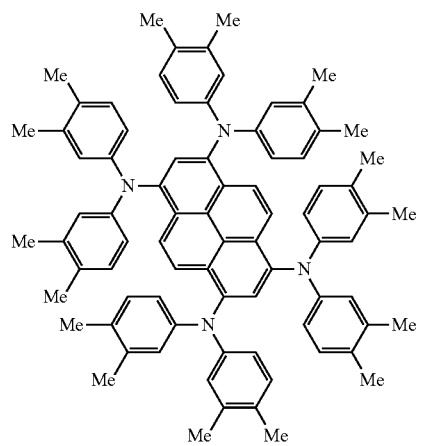
(63)
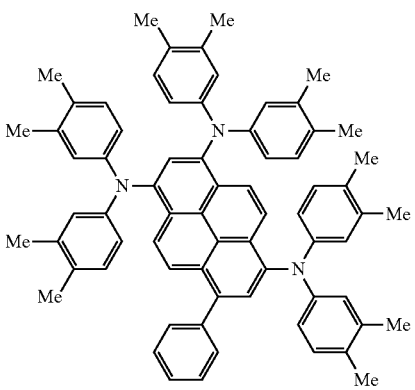
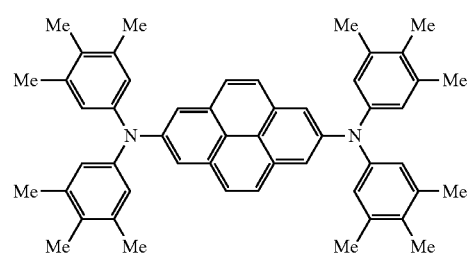
(65)
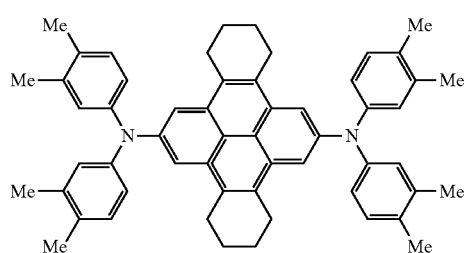
(66)
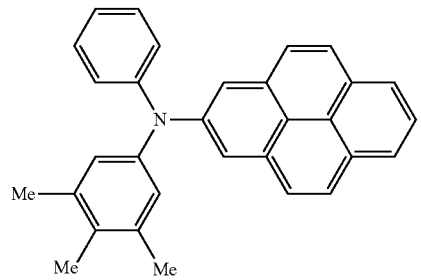
(67)
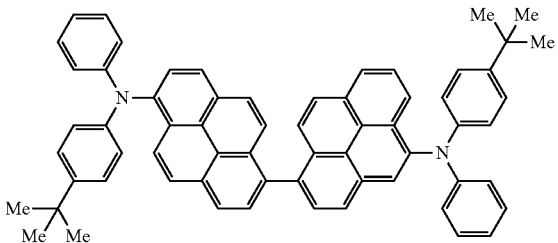

-continued

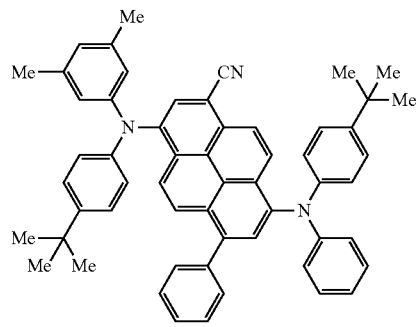

(68)

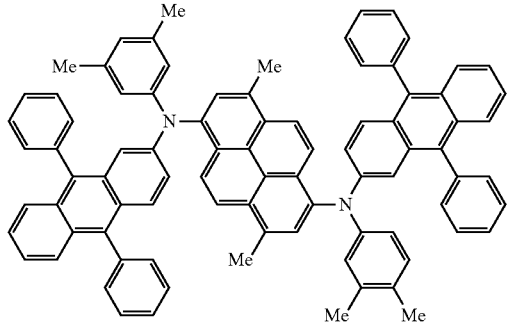

(69)

In the aromatic amine derivative represented by any of the general formulae (I) to (III) and (I') to (III'), since the diphenylamino group having a substituent group is bonded to the pyrene structure, the association between the compounds is prevented, resulting in a prolonged life thereof. Further, the aromatic amine derivatives have a strong fluorescence in a solid state, and are excellent in field light emission, which leads to a fluorescent quantum efficiency as high as 0.3 or more. In addition, the aromatic amine derivatives of the present invention exhibit not only excellent capabilities of injecting and transporting holes from the metal electrode or organic thin film layers, but also excellent capabilities of injecting and transporting electrons from the metal electrode or organic thin film layers and, therefore, are usefully usable as light emitting materials for organic EL devices. Besides, the aromatic amine derivatives of the present invention may be used together with other hole transporting materials, electron transporting materials or doping materials.

The organic EL device of the present invention includes an anode, a cathode, and one or plural organic thin film layers. In the case of one layer type, a light emitting layer as the organic thin film layer is provided between the anode and cathode. The light emitting layer contains the light emitting material and may further contain a hole injecting material and an electron injecting material in order to effectively transport holes injected from the anode or electrons injected from the cathode to the light emitting material. The aromatic amine derivatives represented by the general formulae (I) to (III) and (I') to (III') have a high light emitting property and excellent hole injectability and hole transportability as well as excellent electron injectability and electron transportability and, therefore, can be used as a light emitting material in the light emitting layer.

In the organic EL device of the present invention, the light emitting layer contains the aromatic amine derivative of the present invention in an amount of preferably 0.1 to 20% by weight and more preferably 1 to 10% by weight. Further, the aromatic amine derivatives of the present invention which are represented by the general formulae (I) to (III) and (I') to (III') exhibit not only an extremely high fluorescent quantum efficiency but also high hole transportability and electron transportability, and further are capable of forming a uniform thin film, so that the light emitting layer may be formed from the aromatic amine derivatives only.

On the other hand, in the case where the organic EL device of the present invention includes two or more organic thin film layers having at least the light emitting layer which are sandwiched between the cathode and anode, the organic thin film layers preferably include an organic layer containing the aromatic amine derivative represented by any of the general formulae (I) to (III) and (I') to (III') as a main component which is provided between the anode and the light emitting layer. Such an organic layer may be a hole injecting layer, a hole transporting layer, etc.

Examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The light emitting layer may also optionally contain, in addition to the aromatic amine derivatives of the present invention, conventionally known materials such as light emitting materials, doping materials, hole injecting materials and electron injecting materials according to requirements. The organic EL device having such a multilayer structure can be prevented from suffering from deterioration in luminance and service life due to quenching. If required, the light emitting materials, doping materials, hole injecting materials and electron injecting materials may be used in combination with each other. The use of the doping materials enables the resultant device to be improved in luminance of light emitted and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multi-layer hole injecting layer may include a hole injecting layer into which holes are injected from the electrode, and a hole transporting layer for accepting the holes from the hole injecting layer and transporting the holes to the light emitting layer. Also, the multi-layer electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

Examples of the light emitting material or doping material that is usable in the light emitting layer together with any of the aromatic amine derivatives represented by the above general formulae (I) to (III) and (I') to (III') according to the present invention include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenyl butadiene, tetraphenyl butadiene, coumarin, oxadiazole, aldazine, bis-benzoxazoline, bisstyryl, pyrazine, cyclopentadiene, quinoline metal complexes, aminoquinoline metal complexes, benzoquinoline metal complexes, imines, diphenyl ethylene, vinyl anthracene, diaminocarbazole, pyrane, thiopyrane, polymethine, merocyanine, imidazole-chelated oxinoid compounds, quinacridone, rubrene and fluorescent dyes, though not particularly limited thereto.

The hole injecting material is preferably made of compounds which have a good hole transportability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazole thione, pyrazoline, pyrazolone, tetrahydroimidazole, hydrazone, acyl hydrazone, polyaryl alkanes, stilbene, butadiene, benzidine-type triphenyl amine, styryl amine-type triphenyl amine, diamine-type triphenyl amine and derivatives thereof, as well as polyvinyl carbazoles, polysilanes, and high molecular materials such as conductive polymers, though not particularly limited thereto.

Of these hole injecting materials usable in the organic EL device of the present invention, more effective hole injecting materials are aromatic tertiary amine derivatives and phthalocyanine derivatives.

Specific examples of the aromatic tertiary amine derivatives include triphenyl amine, tritolyl amine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, GaPc-O-GaPc, as well as naphthalocyanine derivatives, though not particularly limited thereto.

Also, in the organic EL device of the present invention, between the light emitting layer and the anode, there is preferably provided a layer containing these aromatic tertiary amine derivatives and/or phthalocyanine derivatives, such as the above hole transporting layer or hole injecting layer.

The electron injecting material is preferably made of compounds which have a good electron transportability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyrane dioxide, oxazole, oxadiazole, triazole, imidazole, perylenetetracarboxylic acid, fluorenylidene methane, anthrone, and derivatives thereof, though not particularly limited thereto. Further, an electron accepting substance and an electron donating substance may be added to the hole injecting material and the electron injecting material, respectively, for enhanced sensitization thereof.

In the organic EL device of the present invention, among these electron injecting materials, more effective electron injecting materials are metal complex compounds and nitrogen-containing five-membered ring derivatives.

Specific examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato)(1-naphtholato) aluminum, and bis(2-methyl-8-quinolinato)(2-naphtholato) gallium, though not particularly limited thereto.

The nitrogen-containing five membered ring derivatives are preferably derivatives of oxazole, thiazole, oxadiazole, thiadiazole or triazole. Specific examples of the nitrogen-containing five membered ring derivatives include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4''-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4''-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4''-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to the aromatic amine derivatives represented by the general formulae (I) to (III) and (I') to (III'), at least one material selected from the group consisting of light emitting materials, doping materials, hole injecting materials and electron injecting materials. The organic EL device of the present invention may be further provided on a surface thereof with a protective layer, or the whole part thereof may be protected with silicone oil, resins, etc., in order to enhance a stability thereof against temperature, humidity, atmosphere, etc.

The anode of the organic EL device according to the present invention may be suitably made of a conductive material having a work function more than 4 eV. Examples of the conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic conductive resins such as polythiophene and polypyrrole. The cathode of the organic EL device according to the present invention may be suitably made of a conductive material having a work function of 4 eV or less. Examples of the conductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is formed using the above conductive material by vapor deposition method, sputtering method, etc., so as to ensure a desirable transparency thereof. The electrode disposed on a light emitting surface of the device preferably has a light transmittance of 10% or more. The substrate is not particularly limited as long as it suitably has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluororethylene-hexafluoropropylene copolymer, polychlorotrifluoroethylene, polyvinylidene fluoride, polyesters, polycarbonates, polyurethanes, polyimides, and polyether imides.

The respective layers of the organic EL device of the present invention may be formed by either a dry film-forming method such as vacuum deposition, sputtering, plasma and ion-plating, or a wet film-forming method such as spin-coating, dipping and flow-coating. The thickness of the respective layers is not particularly limited, but should be adjusted to an appropriate range. If the thickness is too large, a large electric voltage must be applied to the device in order to achieve a predetermined light output, resulting in a poor efficiency of light emission. On the other hand, if the thickness is too small, pinholes tend to be formed in the layers, thereby failing to obtain a sufficient luminance of light emitted even upon applying an electric field thereto. The suitable thickness of the respective layers is usually in the range of from 5 nm to 10 μm and preferably from 10 nm to 0.2 μm.

In the wet film-forming method, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethyl methacrylate, polymethyl acrylate and celluloses as well as copolymers thereof, photoconductive resins such as poly-N-vinyl carbazole and polysilanes, and conductive resins such as polythiophene and polypyrrole. Examples of the additives include antioxidants, ultraviolet absorbers and plasticizers.

As described above, by using the aromatic amine derivative of the present invention in organic thin film layers of the organic EL device, the obtained organic EL device can exhibit a long life and a high efficiency of light emission.

The organic EL device of the present invention is suitably applied to, for example, surface light-emitting members such as a wall-type TV flat panel displays, light sources for copiers, printers, back light for liquid crystal displays and, measuring equipments, display panels, marker light, etc. Further, the material of the present invention can be used not only for organic EL devices but also in other applications such as electrophotographic members, photoelectric converters, solar cells, image sensors, etc. The present invention will be described in more detail by reference to the following examples. However, it should be noted that these examples are only illustrative and not intended to limit the invention thereto.

Synthesis Example 1

Synthesis of Compound (8)

Under an argon gas flow, 3.6 g (10 mmol) of 1,6-dibromopyrene, 5.2 g (25 mmol) of 4-isopropyl diphenyl amine, 0.03 g (1.5 mol %) of palladium acetate, 0.06 g (3 mol %) of tri-t-butyl phosphine, 2.4 g (25 mmol) of t-butoxy sodium and 100 milliliter of dried toluene were charged into a three-necked flask having a capacity of 300 milliliter and equipped with a condenser, and then stirred under heating at a temperature of 100° C. over night. After completion of the reaction, the precipitated crystals were separated from the reaction solution by filtration, and then washed with 50 milliliter of toluene and 100 milliliter of methanol, thereby obtaining 5.5 g of a light-yellow powder. The thus obtained powder was subjected to NMR spectrum analysis (FIG. 1) and FD-MS (field-desorption mass spectrum analysis). As a result, the reaction product was identified as Compound (8) (yield: 89%).

Meanwhile, the NMR spectrum was measured by Fourier-transform Nuclear Magnetic Resonance analyzer "R-1900" (90 MHz) produced by Hitachi, Ltd., using $CDCl_3$ as a solvent.

Synthesis Example 2

Synthesis of Compound (9)

Figure 2:
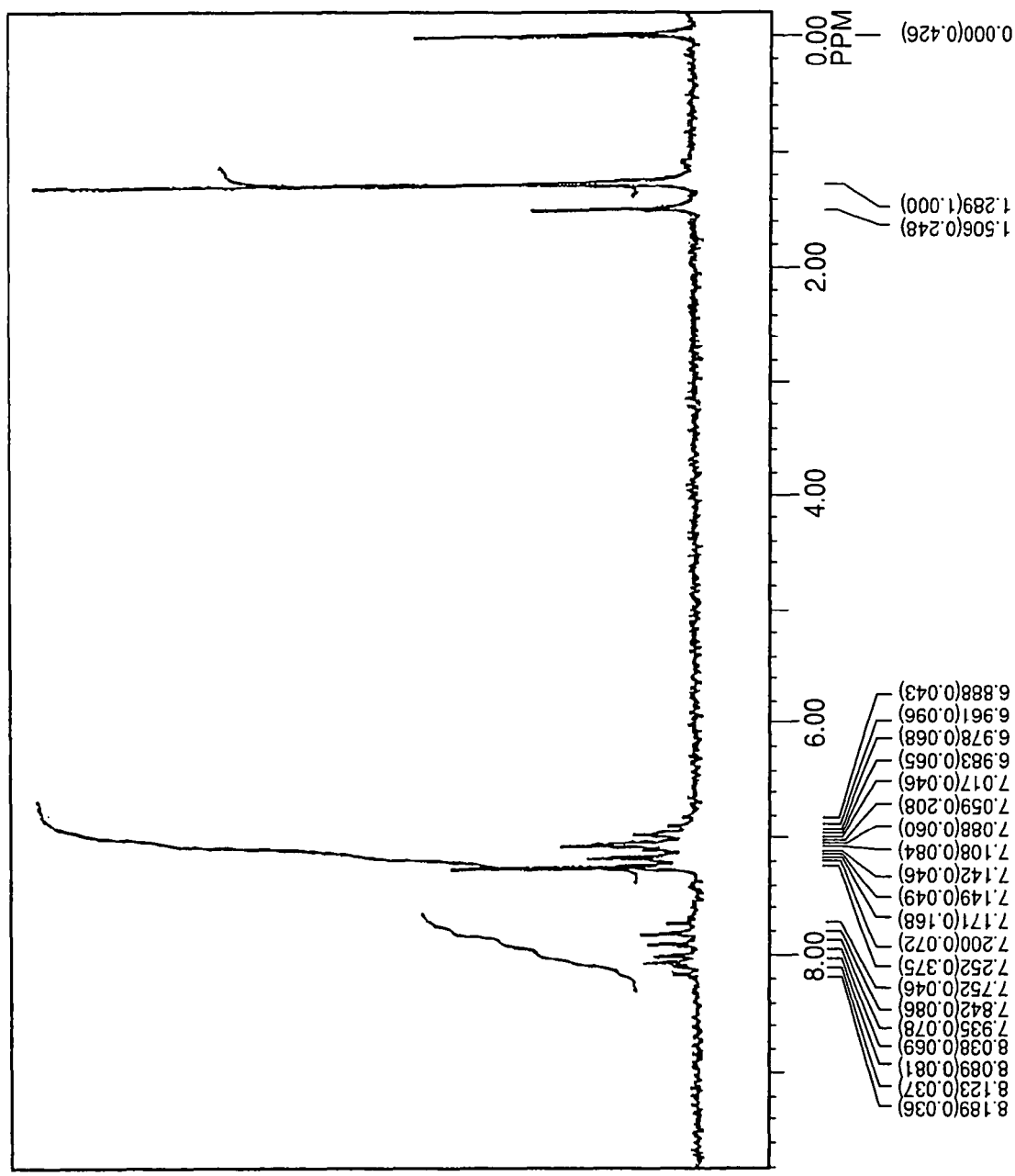
FIG. 2 is a chart showing NMR spectrum of the compound (9) as the aromatic amine derivative of the present invention.

Under an argon gas flow, 3.6 g (10 mmol) of 1,6-dibromopyrene, 5.6 g (25 mmol) of 4-t-butyl diphenyl amine, 0.03 g (1.5 mol %) of palladium acetate, 0.06 g (3 mol %) of tri-t-butyl phosphine, 2.4 g (25 mmol) of t-butoxy sodium and 100 milliliter of dried toluene were charged into a three-necked flask having a capacity of 300 milliliter and equipped with a condenser, and then stirred under heating at a temperature of 100° C. over night. After completion of the reaction, the precipitated crystals were separated from the reaction solution by filtration, and then washed with 50 milliliter of toluene and 100 milliliter of methanol, thereby obtaining 5.1 g of a light-yellow powder. The thus obtained powder was subjected to NMR spectrum analysis (FIG. 2) and FD-MS. As a result, the reaction product was identified as Compound (9) (yield: 79%). Meanwhile, the NMR spectrum was measured by the same method as described in SYNTHESIS EXAMPLE 1.

Synthesis Example 3

Synthesis of Compound (12)

Figure 3:
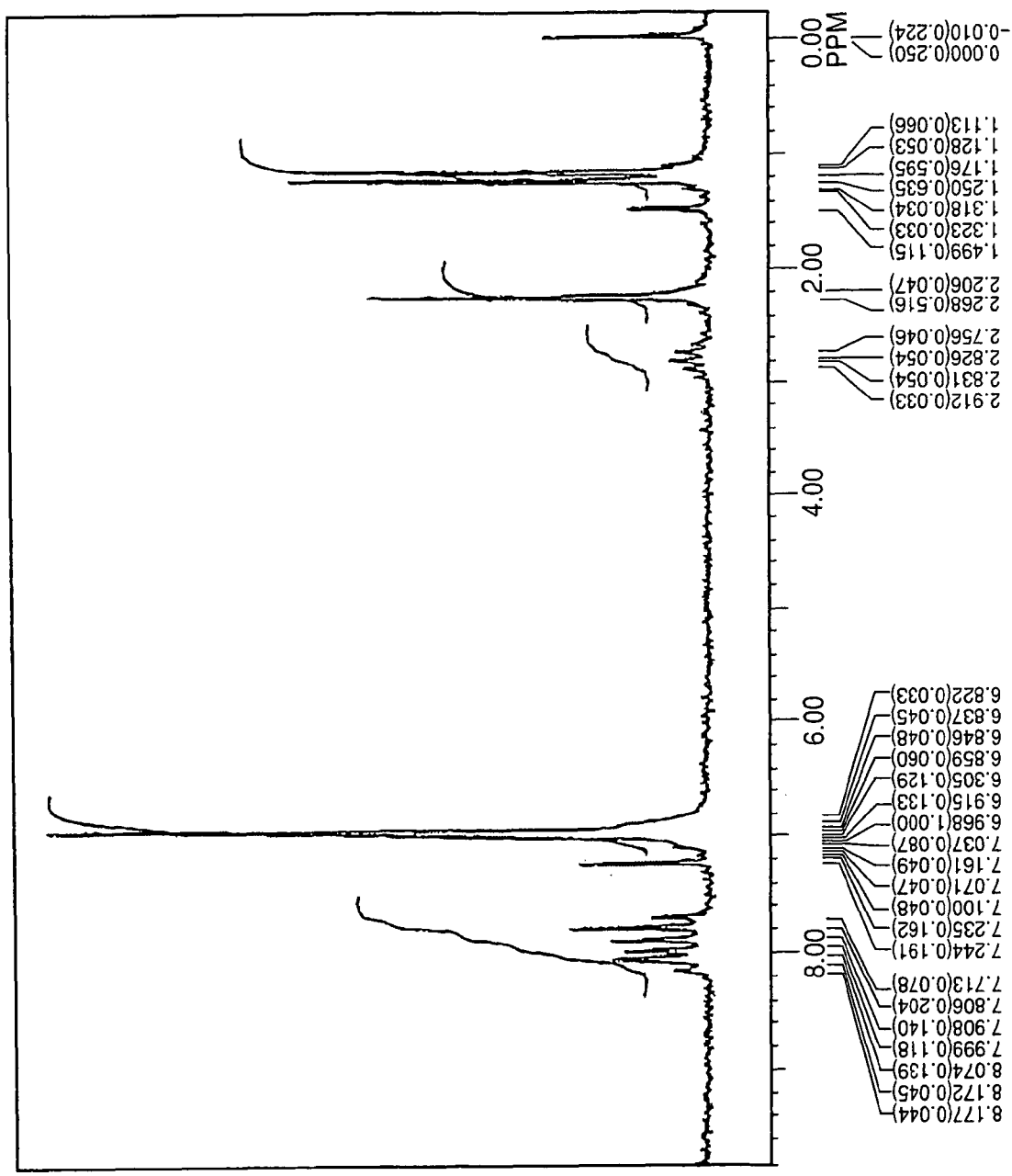
FIG. 3 is a chart showing NMR spectrum of the compound (12) as the aromatic amine derivative of the present invention.

Under an argon gas flow, 3.6 g (10 mmol) of 1,6-dibromopyrene, 4.9 g (25 mmol) of 4-isopropylphenyl-p-tolylamine, 0.03 g (1.5 mol %) of palladium acetate, 0.06 g (3 mol %) of tri-t-butyl phosphine, 2.4 g (25 mmol) of t-butoxy sodium and 100 milliliter of dried toluene were charged into a three-necked flask having a capacity of 300 milliliter and equipped with a condenser, and then stirred under heating at a temperature of 100° C. over night. After completion of the reaction, the precipitated crystals were separated from the reaction solution by filtration, and then washed with 50 milliliter of toluene and 100 milliliter of methanol, thereby obtaining 5.7 g of a light-yellow powder. The thus obtained powder was subjected to NMR spectrum analysis (FIG. 3) and FD-MS. As a result, the reaction product was identified as Compound (12) (yield: 93%). Meanwhile, the NMR spectrum was measured by the same method as described in SYNTHESIS EXAMPLE 1.

Synthesis Example 4

Synthesis of Compound (13)

Figure 4:
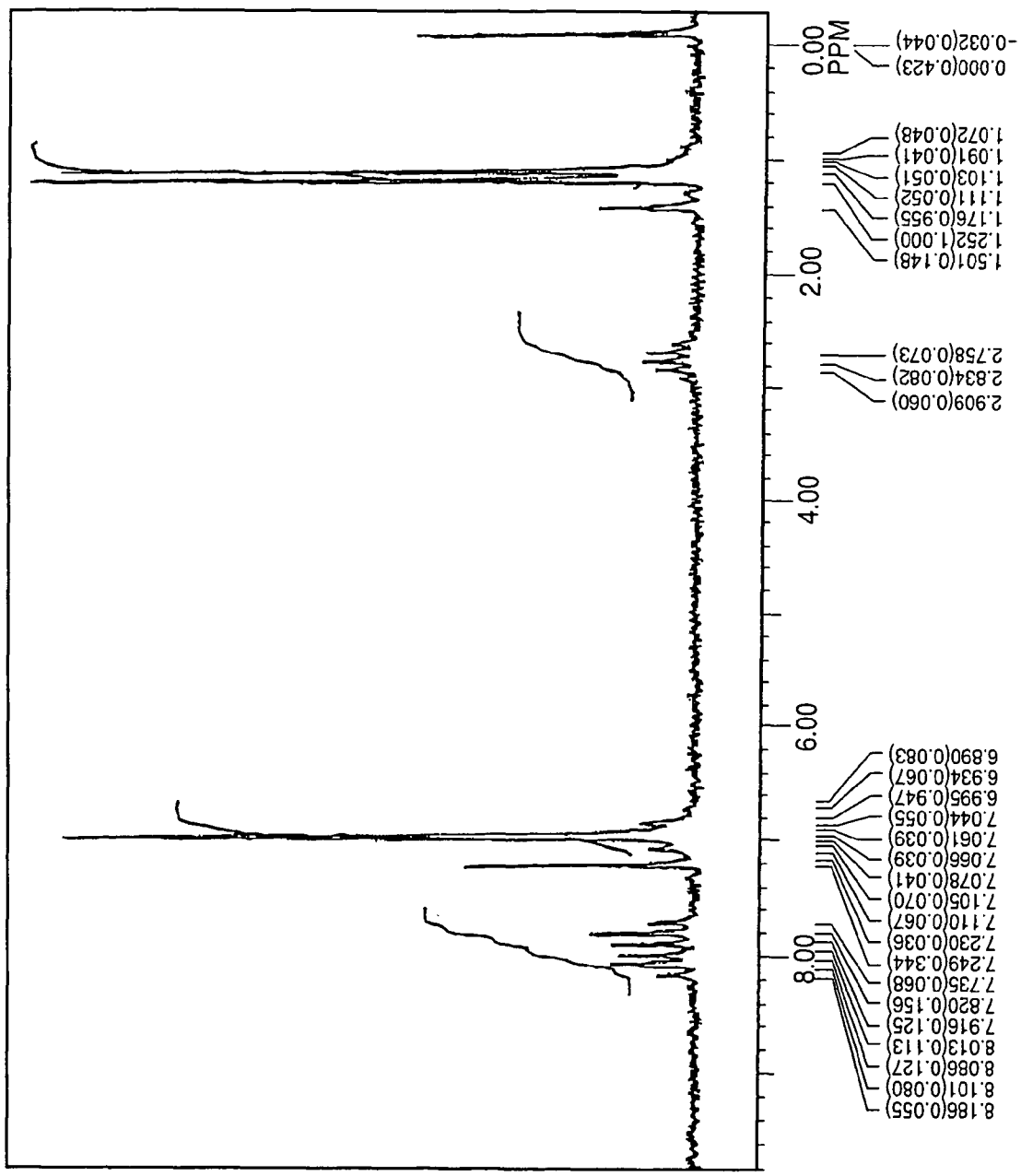
FIG. 4 is a chart showing NMR spectrum of the compound (13) as the aromatic amine derivative of the present invention.

Under an argon gas flow, 3.6 g (10 mmol) of 1,6-dibromopyrene, 6.3 g (25 mmol) of bis(4-isopropylphenyl)amine, 0.03 g (1.5 mol %) of palladium acetate, 0.06 g (3 mol %) of tri-t-butyl phosphine, 2.4 g (25 mmol) of t-butoxy sodium and 100 milliliter of dried toluene were charged into a three-necked flask having a capacity of 300 milliliter and equipped with a condenser, and then stirred under heating at a temperature of 100° C. over night. After completion of the reaction, the precipitated crystals were separated from the reaction solution by filtration, and then washed with 50 milliliter of toluene and 100 milliliter of methanol, thereby obtaining 7.1 g of a light-yellow powder. The thus obtained powder was subjected to NMR spectrum analysis (FIG. 4) and FD-MS. As a result, the reaction product was identified as Compound (13) (yield: 97%). Meanwhile, the NMR spectrum was measured by the same method as described in SYNTHESIS EXAMPLE 1.

Synthesis Example 5

Synthesis of Compound (52)

Figure 5:
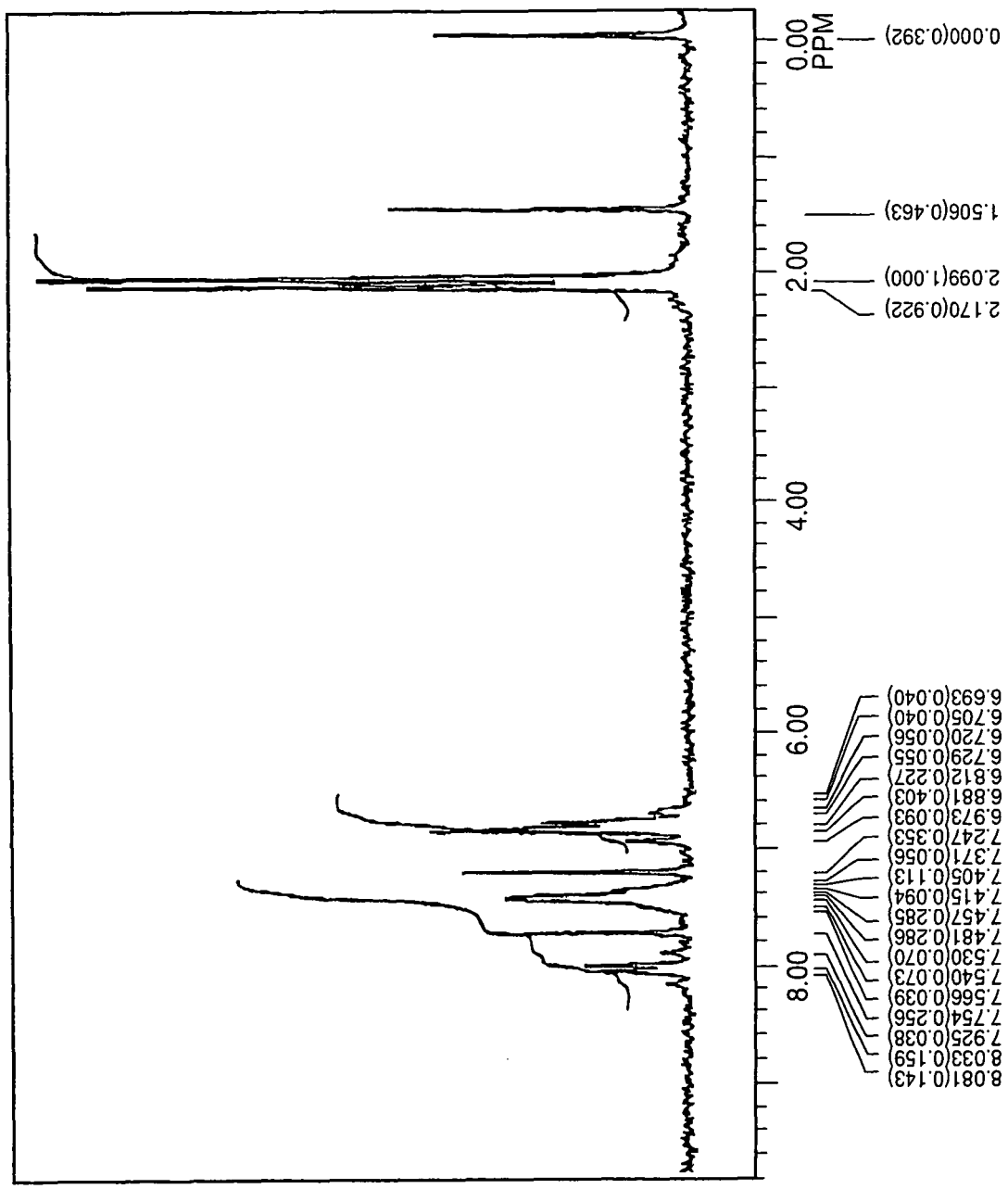
FIG. 5 is a chart showing NMR spectrum of the compound (52) as the aromatic amine derivative of the present invention.

Under an argon gas flow, 3.6 g (10 mmol) of 1,6-dibromopyrene, 5.6 g (25 mmol) of bis(3,4-dimethylphenyl)amine, 0.03 g (1.5 mol %) of palladium acetate, 0.06 g (3 mol %) of tri-t-butyl phosphine, 2.4 g (25 mmol) of t-butoxy sodium and 100 milliliter of dried toluene were charged into a three-necked flask having a capacity of 300 milliliter and equipped with a condenser, and then stirred under heating at a temperature of 100° C. over night. After completion of the reaction, the precipitated crystals were separated from the reaction solution by filtration, and then washed with 50 milliliter of toluene and 100 milliliter of methanol, thereby obtaining 5.9 g of a light-yellow powder. The thus obtained powder was subjected to NMR spectrum analysis (FIG. 5) and FD-MS. As a result, the reaction product was identified as Compound (52) (yield: 92%). Meanwhile, the NMR spectrum was measured by the same method as described in SYNTHESIS EXAMPLE 1.

Synthesis Example 6

Synthesis of Compound (59)

Figure 6:
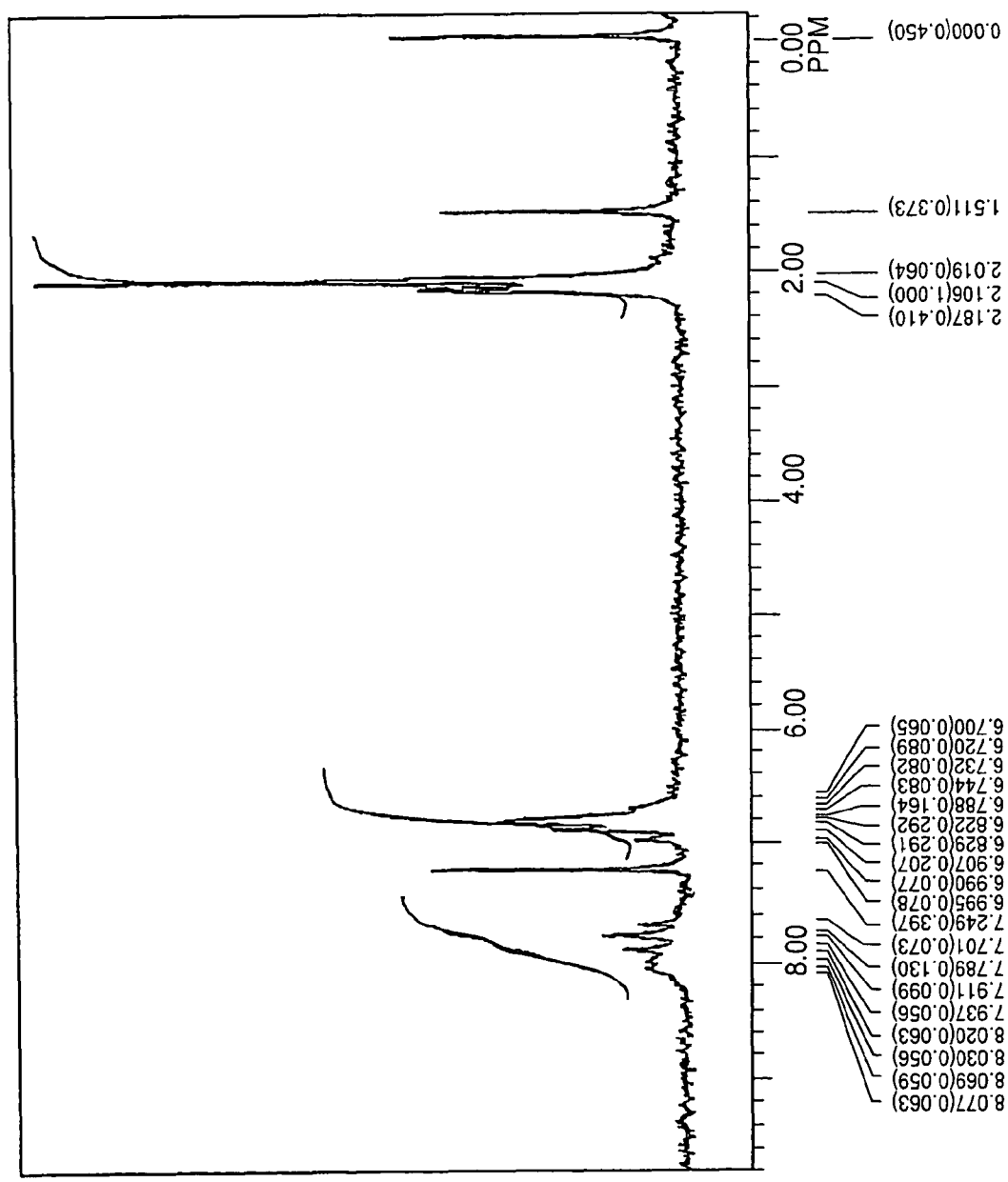
FIG. 6 is a chart showing NMR spectrum of the compound (59) as the aromatic amine derivative of the present invention.

Under an argon gas flow, 5.1 g (10 mmol) of 1,6-dibromo-3,8-diphenylpyrene, 5.6 g (25 mmol) of bis(3,4-dimethylphenyl)amine, 0.03 g (1.5 mol %) of palladium acetate, 0.06 g (3 mol %) of tri-t-butyl phosphine, 2.4 g (25 mmol) of t-butoxy sodium and 100 milliliter of dried toluene were charged into a three-necked flask having a capacity of 300 milliliter and equipped with a condenser, and then stirred under heating at a temperature of 100° C. over night. After completion of the reaction, the precipitated crystals were separated from the reaction solution by filtration, and then washed with 50 milliliter of toluene and 100 milliliter of methanol, thereby obtaining 7.0 g of a light-yellow powder. The thus obtained powder was subjected to NMR spectrum analysis (FIG. 6) and FD-MS. As a result, the reaction product was identified as Compound (59) (yield: 88%). Meanwhile, the NMR spectrum was measured by the same method as described in SYNTHESIS EXAMPLE 1.

Example 1

A 120 nm-thick transparent electrode made of indium oxide was formed on a glass substrate having a size of 25 mm×75 mm×1.1 mm. The glass substrate with the transparent electrode was cleaned by irradiation of UV and ozone. The thus cleaned glass substrate with the transparent electrode was mounted to a vacuum vapor deposition apparatus.

First, N',N"-bis[4-(diphenylamino)phenyl]-N',N"'-diphenylbiphenyl-4,4'-diamine was vapor-deposited to form a hole injecting layer having a thickness of 60 nm, and then N,N,N',N'-tetrakis(4-biphenyl)-4,4'-bendizine was vapor-deposited on the hole injecting layer to form a hole transporting layer having a thickness of 20 nm. Then, 10,10'-bis[1,1',4',1"]terphenyl-2-yl-9,9'-bianthracenyl and the above Compound (12) were simultaneously vapor-deposited at a weight ratio of 40:2 on the hole transporting layer to form a light emitting layer having a thickness of 40 nm.

Next, tris(8-hydroxyquinolinato)aluminum was vapor-deposited on the light emitting layer to form an electron injecting layer having a thickness of 10 nm. Then, tris(8-hydroxyquinolinato)aluminum and lithium was vapor-deposited at a weight ratio of 10:0.3 on the electron injecting layer to form a layer having a thickness of 10 nm, and further aluminum was vapor-deposited thereon to form an aluminum layer having a thickness of 150 nm. The aluminum layer functioned as a cathode. Thus, an organic EL device was produced.

As a result of subjecting the thus obtained organic EL device to a test by passing electric current, it was confirmed that a blue light with a luminance of 938 $cd/m^2$ (peak wavelength of light emission: 476 nm) was emitted at a voltage of 6.9 V and a current density of 10 $mA/cm^2$. Further, as a result of subjecting the device to a continuous test by passing DC electric current starting at an initial luminance of 3000 $cd/m^2$, it was confirmed that the half lifetime thereof was 2000 hrs.

Example 2

The same procedure as in EXAMPLE 1 was repeated except for using Compound (13) in place of Compound (12), thereby producing an organic EL device.

As a result of subjecting the thus obtained organic EL device to the test by passing electric current, it was confirmed that a blue light with a luminance of 970 $cd/m^2$ (peak wavelength of light emission: 477 nm) was emitted at a voltage of 6.9 V and a current density of 10 $mA/cm^2$. Further, as a result of subjecting the device to the continuous test by passing DC electric current starting at an initial luminance of 3000 $cd/m^2$, it was confirmed that the half lifetime thereof was 2100 hrs.

Comparative Example 1

The same procedure as in EXAMPLE 1 was repeated except for using 1,6-bis(p,p'-ditolylamino)pyrene in place of Compound (12), thereby producing an organic EL device.

As a result of subjecting the thus obtained organic EL device to the test by passing electric current, it was confirmed that a blue light with a luminance of 976 $cd/m^2$ (peak wavelength of light emission: 477 nm) was emitted at a voltage of 6.8 V and a current density of 10 mA/cm². Further, as a result of subjecting the device to the continuous test by passing DC electric current starting at an initial luminance of 3000 cd/m², it was confirmed that the half lifetime thereof was as short as 900 hrs.

Comparative Example 2

The same procedure as in EXAMPLE 1 was repeated except for using 1,4-bis[(2-{4-diphenylamino}phenyl)vinyl]benzene in place of Compound (12), thereby producing an organic EL device.

As a result of subjecting the thus obtained organic EL device to the test by passing electric current, it was confirmed that a blue light with a luminance of 809 cd/m² (peak wavelength of light emission: 468 nm) was emitted at a voltage of 6.4 V and a current density of 10 mA/cm². Further, as a result of subjecting the device to the continuous test by passing DC electric current starting at an initial luminance of 3000 cd/m², it was confirmed that the half lifetime thereof was as short as 1000 hrs.

INDUSTRIAL APPLICABILITY

The organic EL device using the aromatic amine derivative represented by any of the general formulae (I) to (III) and (I') to (III') according to the present invention can exhibit a practically sufficient luminance of light emitted even upon applying a low voltage thereto, and has a high efficiency of light emission and the device is free from deterioration in properties even after being used for a long period of time and, therefore, has a long lifetime.

The invention claimed is:

1. An organic electroluminescent device, comprising an aromatic amine derivative represented by the following general formula (II') as a light emitting material:

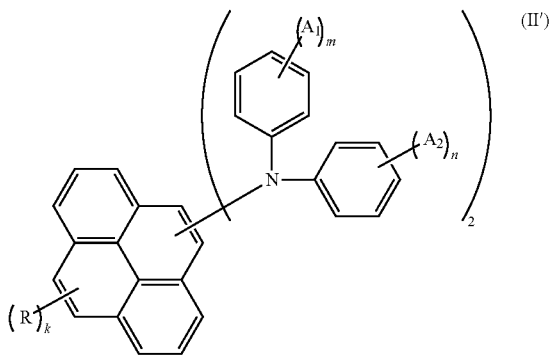

wherein:
R is a substituted or unsubstituted alkyl group having 1 to 50 carbon atoms, a substituted or unsubstituted aryl group having 5 to 50 carbon atoms, a substituted or unsubstituted cycloalkyl group having 3 to 50 carbon atoms, a cyano group or a halogen atom;
k is an integer of 0 to 8;
when k is 2 or more, a plurality of R groups may be the same with or different from each other;
$A_1$ is an unsubstituted alkyl group having 1 to 50 carbon atoms, a substituted or unsubstituted aryl group having 5 to 50 carbon atoms, an unsubstituted cycloalkyl group having 3 to 50 carbon atoms, a cyano group or a halogen atom;
$A_2$ is an unsubstituted alkyl group having 1 to 50 carbon atoms, a substituted or unsubstituted aryl group having 5 to 50 carbon atoms, an unsubstituted cycloalkyl group having 3 to 50 carbon atoms, a cyano group or a halogen atom;
m is an integer of 2 to 5;
n is an integer of 0 to 5;
a plurality of $A_1$ groups may be the same with or different from each other;
when n is 2 or more, a plurality of $A_2$ groups may be the same with or different from each other; and
the two groups represented by the following formula:

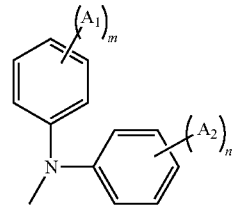

in the general formula (II'), may be the same or different from each other, and bond to the pyrene ring at 1-position and 6-position.

2. The organic electroluminescent device according to claim 1, further comprising:
a cathode;
an anode; and
one or plural organic thin film layers including at least one light emitting layer between the cathode and the anode;
wherein the aromatic amine derivative is present in at least one of the organic thin film layers in the form of a single substance or a component of a mixture.

3. The organic electroluminescent device according to claim 1, further comprising:
a cathode;
an anode; and
two or more organic thin film layers including at least one light emitting layer between the cathode and the anode;
wherein the aromatic amine derivative is present as a main component in an organic thin film layer between the anode and the light emitting layer.

4. The organic electroluminescent device according to claim 2, wherein the light emitting layer contains the aromatic amine derivative in an amount of 0.1 to 20% by weight.

5. The organic electroluminescent device according to claim 1, wherein:
m is 2 or 3; and
n is 0.

6. The organic electroluminescent device according to claim 1, wherein each $A_1$ is selected from the group consisting of unsubstituted methyl, unsubstituted ethyl, unsubstituted propyl, unsubstituted isopropyl, substituted or unsubstituted phenyl, substituted or unsubstituted biphenyl, substituted or unsubstituted terphenyl, substituted or unsubstituted naphthyl, fluorine, chlorine, and bromine.

7. The organic electroluminescent device according to claim 1, wherein each $A_2$ is selected from the group consisting of unsubstituted methyl, unsubstituted ethyl, unsubstituted propyl, unsubstituted isopropyl, substituted or unsubstituted phenyl, substituted or unsubstituted biphenyl, substituted or unsubstituted terphenyl, substituted or unsubstituted naphthyl, fluorine, chlorine, and bromine.

8. The organic electroluminescent device according to claim 1, wherein each R is selected from the group consisting of unsubstituted methyl, unsubstituted ethyl, unsubstituted propyl, unsubstituted isopropyl, substituted or unsubstituted phenyl, substituted or unsubstituted biphenyl, substituted or unsubstituted terphenyl, substituted or unsubstituted naphthyl, fluorine, chlorine, and bromine.

9. The organic electroluminescent device according to claim 1, wherein the two groups represented by the following formula:

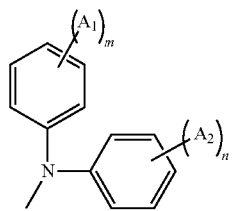

in the general formula (II') are the same.

10. The organic electroluminescent device according to claim 9, wherein m is 2 or 3.

11. The organic electroluminescent device according to claim 10, wherein each $A_1$ is an unsubstituted methyl, a substituted or unsubstituted phenyl, fluorine, or chlorine.

12. The organic electroluminescent device according to claim 11, wherein each $A_1$ is an unsubstituted methyl, an unsubstituted phenyl, fluorine, or chlorine.

13. The organic electroluminescent device according to claim 11, wherein each $A_2$ is an unsubstituted methyl, an unsubstituted phenyl, fluorine, or chlorine.

14. The organic electroluminescent device according to claim 11, wherein n is 2.

15. The organic electroluminescent device according to claim 14, wherein each $A_2$ is unsubstituted methyl.

16. The organic electroluminescent device according to claim 15, wherein k is 0.

17. The organic electroluminescent device according to claim 15, wherein k is 2.

18. The organic electroluminescent device according to claim 17, wherein each R is unsubstituted phenyl.

* * * * *